(12) United States Patent
Gold et al.

(10) Patent No.: US 7,897,389 B2
(45) Date of Patent: *Mar. 1, 2011

(54) DIRECT DIFFERENTIATION METHOD FOR MAKING CARDIOMYOCYTES FROM HUMAN EMBRYONIC STEM CELLS

(75) Inventors: Joseph D. Gold, San Francisco, CA (US); Mohammad Hassanipour, Danville, CA (US); Lila R. Collins, Fremont, CA (US); Chunhui Xu, Palo Alto, CA (US)

(73) Assignee: Geron Corporation, Menlo Park, CA (US)

(*) Notice: Subject to any disclaimer, the term of this patent is extended or adjusted under 35 U.S.C. 154(b) by 109 days.

This patent is subject to a terminal disclaimer.

(21) Appl. No.: 12/210,779

(22) Filed: Sep. 15, 2008

(65) Prior Publication Data

US 2009/0047739 A1 Feb. 19, 2009

(51) Int. Cl.
C12N 5/00 (2006.01)
C12N 5/02 (2006.01)
C12N 5/07 (2006.01)
C12N 5/10 (2006.01)

(52) U.S. Cl. .................. 435/377; 435/383; 435/384; 435/363

(58) Field of Classification Search ................ 435/377, 435/383, 384, 363
See application file for complete search history.

(56) References Cited

U.S. PATENT DOCUMENTS

| | | | |
|---|---|---|---|
| 5,543,318 A | 8/1996 | Smith et al. | |
| 5,733,727 A | 3/1998 | Field | |
| 5,843,780 A | 12/1998 | Thomson | |
| 5,928,943 A | 7/1999 | Franz et al. | |
| 6,015,671 A | 1/2000 | Field | |
| 6,099,832 A | 8/2000 | Mickle et al. | |
| 6,110,459 A | 8/2000 | Mickle et al. | |
| 6,245,566 B1 | 6/2001 | Gearhart et al. | |
| 6,261,836 B1 | 7/2001 | Cech et al. | |
| 6,387,369 B1 | 5/2002 | Pittenger et al. | |
| 6,399,300 B1 | 6/2002 | Field | |
| 6,534,052 B1 | 3/2003 | Xiao et al. | |
| 7,425,448 B2 | 9/2008 | Xu | |
| 7,452,718 B2 | 11/2008 | Gold et al. | |
| 2002/0061837 A1 | 5/2002 | Lough, Jr. et al. | |
| 2002/0142457 A1 | 10/2002 | Umezawa et al. | |
| 2002/0146678 A1 | 10/2002 | Benvenisty | |
| 2004/0005701 A1 | 1/2004 | Xu et al. | |
| 2004/0022367 A1 | 2/2004 | Talalai | |
| 2005/0037489 A1 | 2/2005 | Gepstein et al. | |
| 2005/0054092 A1 | 3/2005 | Xu et al. | |
| 2005/0164382 A1 | 7/2005 | Xu | |
| 2005/0214938 A1 | 9/2005 | Xu et al. | |
| 2005/0227353 A1 | 10/2005 | Mummery | |
| 2005/0266554 A1 | 12/2005 | D'Amour et al. | |
| 2009/0017465 A1 | 1/2009 | Xu | |
| 2009/0047739 A1 | 2/2009 | Xu et al. | |

FOREIGN PATENT DOCUMENTS

| | | |
|---|---|---|
| AU | 729377 B2 | 2/2001 |
| WO | WO 92/13066 A1 | 8/1992 |
| WO | WO 95/14079 A1 | 5/1995 |
| WO | WO 99/49015 A2 | 9/1999 |
| WO | WO 00/06701 A1 | 2/2000 |
| WO | WO 00/70021 A2 | 11/2000 |
| WO | WO 00/78119 A2 | 12/2000 |
| WO | WO 01/22978 A2 | 4/2001 |
| WO | WO 01/48151 A1 | 7/2001 |
| WO | WO 01/51616 A2 | 7/2001 |
| WO | WO 01/53465 A1 | 7/2001 |
| WO | WO 01/68814 A2 | 9/2001 |
| WO | WO 02/09650 A2 | 2/2002 |
| WO | WO-02/10347 | 2/2002 |
| WO | WO 02/13760 A2 | 2/2002 |
| WO | WO 02/19893 A2 | 3/2002 |
| WO | WO 02/30206 A1 | 4/2002 |
| WO | WO 02/083864 A1 | 10/2002 |
| WO | WO 03/006950 A2 | 1/2003 |
| WO | WO-03/087296 | 10/2003 |
| WO | WO 2004/081205 A1 | 9/2004 |

OTHER PUBLICATIONS

Ginis, I. et al., "Differences between human and mouse embryonic stem cells", *Dev. Biol.* 269 (2004), 360-80.
Goldman, B. et al., "Human fetal cardiocytes in enriched culture", In Vitro *Cell. Dev. Biol.—Animal* 31 (1995), 731-4.
Goldman, B. et al., "Epidermal growth factor promotes a cardiomyoblastic phenotype in human fetal cardiac myocytes," *Exp. Cell Res.* 228:237-45 (1996).
Piao, S. et al., "A simplified method for identification of human cardiac myosin heavy-chain isoforms," *Biotechnol. Appl. Biochem.* 37:27-30 (2003).
Boheler, K. et al., "Differentiation of pluripotent embryonic stem cells into cardiomyocytes," *Circ. Res.* 91:189-201 (2002).
De Pater, E. et al., "Distinct phases of cardiomyocyte differentiation regulate growth of the zebrafish heart," *Development* 136:1633-41 (2009).

(Continued)

Primary Examiner—Thaian N Ton
(74) Attorney, Agent, or Firm—E. Stewart Mittler

(57) ABSTRACT

This invention provides a new procedure for generating cardiomyocyte lineage cells from embryonic stem cells for use in regenerative medicine. Differentiating by way of embryoid body formation or in serum is no longer required. Instead, the stem cells are plated onto a solid substrate, and differentiated in the presence of select factors and morphogens. After enrichment for cells with the appropriate phenotype, the cells are allowed to cluster into Cardiac Bodies™, which are remarkably homogeneous and suitable for the treatment of heart disease.

14 Claims, 10 Drawing Sheets

OTHER PUBLICATIONS

Alsan, B. & Schultheiss, T., "Regulation of avian cardiogenesis by Fgf8 signaling," *Develoment* 129:1935-43 (2002).

Andrée, B. et al., "BMP-2 induces ectopic expression of cardiac lineage markers and interferes with somite formation in chicken embryos," *Mech. Dev.* 70:119-31 (1998).

Antin, P. et al., "Regulation of avian precardiac mesoderm development by insulin and insulin-like growth factors," *J. Cell. Physiol.* 168:42-50 (1996).

Arai, A. et al., "Murine cardiac progenitor cells require visceral embryonic endoderm and primitive streak for terminal differentiation," Dev. Dynamics 210:344-53 (1997).

Barron, M. et al., "Requirement for BMP and FGF signaling during cardiogenic induction in non-precardiac mesoderm is specific, transient, and cooperative," *Dev. Dynamics* 218:383-93 (2000).

Bauwens, C. et al., "Development of a perfusion fed bioreactor for embryonic stem cell-derived cardiomyocyte generation: oxygen-mediated enhancement of cardiomyocyte output," *Biotechnol. Bioeng.* 90(4):452-61 (2005).

Behfar, A. et al., "Stem cell differentiation requires a paracrine pathway in the heart," *Faseb J.* 16:1558-66 (2002).

Caspi, O. & Gepstein, L., "Potential applications of human embryonic stem cell-derived cardiomyocytes," *Ann. N. Y. Acad. Sci.* 1015:285-298 (2004).

Charron, F. et al., "Gata transcription factors and cardiac development," *Sem. Cell Dev. Biol.* 10:85-91 (1999).

Claycomb, W. et al., "HL-1 cells: A cardiac muscle cell line that contracts and retains phenotypic characteristics of the adult cardiomyocyte," *Proc. Natl. Acad. Sci. USA* 95:2979-84 (1998).

Czyz, J. et al., "Potential of embryonic and adult stem cells in vitro," *Biol. Chem.* 384:1391-409 (2003).

Dang, S. et al., "Controlled, scalable embryonic stem cell differentiation culture," *Stem Cells* 22:275-82 (2004).

Doevendans, P. et al., "Differentiation of cardiomyocytes in floating embryoid bodies is comparable to fetal cardiomyocytes," *J. Mol. Cell Cardiol.* 32:839-51 (2000).

Dubus, I. et al., "Contractile protein gene expression in serum-free cultured adult rat cardiac myocytes," *Pflügers Arch.* 423:455-61 (1993).

Fukuda, K., "Development of regenerative cardiomyocytes from mesenchymal stem cells for cardiovascular tissue engineering," *Artificial Organs* 25(3):187-93 (2001).

Gepstein, L., "Derivation and potential applications of human embryonic stem cells," *Circ. Res.* 91(10):866-76 (2002).

Gerecht-Nir, S. et al., "Vascular gene expression and phenotypic correlation during differentiation of human embryonic stem cells," *Dev. Dyn.* 232:487-97 (2005).

Goh, G. et al., "Molecular and phenotypic analyses of human embryonic stem cell-derived cardiomyocytes," *Thromb. Haemost.* 94:728-37 (2005).

Grépin, C. et al., "Enhanced cardiogenesis in embryonic stem cells overexpressing the GATA-4 transcription factor," *Development* 124:2387-95 (1997).

Gryshchenko, O. et al., "Outwards currents in embryonic stem cell-derived cardiomyocytes," Pflügers Arch—Eur. J. Physiol. 439:798-807 (2000).

Heng, B. et al., "Strategies for directing the differentiaion of stem cells into the cardiomyogenic lineage in vitro," *Cardiovascular Res.* 62:34-42 (2004).

Itskovitz-Eldor, J. et al., "Differentiation of human embronic stem cells into embryoid bodies comprising the three embryonic germ layers," *Molec. Med.* 6(2):88-95 (2000).

Johansson, B. & Wiles, M., "Evidence for involvement of activin A and bone morphogenetic protein 4 in mammalian mesoderm and hematopoietic development," *Molec. Cell. Biol.* 15(1):141-51 (1995).

Kawai, T. et al., "Efficient cardiomyogenic differentiation of embryonic stem cell by fibroblast growth factor 2 and bone morphogenetic protein 2," *Circ. J.* 68:691-702 (2004).

Kehat, I. et al., "Electromechanical integration of cardiomyocytes derived from human embryonic stem cells," *Nature Biotechnol.* 22(10):1282-89 (2004).

Kehat, I. et al., "Human embryonic stem cells can diffrentiate into myocytes with structural and functional properties of cardiomyocytes," *J. Clin. Invest.* 108(3):407-14 (2001).

Kehat, I. et al., "Long term high-resolution, electrophysiological assessment of human embryonic stem cell derived cardiomyocytes: A novel in vitro model for the human heart," *Circulation* 102(18 Suppl. II):11-4 Abstract 6 (2000).

Kessler, P. & Byrne, B., "Myoblast cell grafting into heart muscle: Cellular biology and potential applications," *Annu. Rev. Physiol.* 61:219-42 (1999).

Khamsi, R. "Geneticists hail variety show, map of DNA differences will help experts tailor drugs," *Nature*, online, 2 pages (Oct. 26, 2005).

Khamsi, R. "Market Watch," *Nature* 437:1231 (2005).

Klug, M. et al., "Genetically selected cardiomyocytes from differentiating embryonic stem cells form stable intracardiac grafts," *J. Clin. Invest.* 98(1):216-24 (1996).

Koide, M. et al., "Atrial natriuretic peptide accelerates proliferation of chick embryonic cardiomyocytes in vitro," *Differentiation* 61:1-11 (1996).

Kolossov, E. et al., "Functional characteristics of ES cell-derived cardiac precursor cells identified by tissue-specific expression of the green fluorescent protein," *J. Cell Biol.* 143(7):2045-56 (1998).

Ladd, A. et al., "Regulation of avian cardiac myogenesis by activin/TGFβ and bone morphogenetic proteins," *Dev. Biology* 204:407-19 (1998).

Laflamme, M. et al., "Formation of human myocardium in the rat heart from human embryonic stem cells," *Am. J. Pathol.* 167(3):663-71 (2005).

Lev, S. et al., "Differentiation pathways in human embryonic stem cell-derived cardiomyocytes," *Ann. N.Y. Acad. Sci.* 1047:50-65 (2005).

Li, R.-K. et al., "Isolation of cardiomyocytes from human myocardium for primary cell culturing," *J. Tiss. Cult. Meth.* 15:147-54 (1993).

Liechty, K. et al., "Human mesenchymal stem cells engraft and demonstrate site-specific differentiation after in utero transplantation in sheep," *Nature Med.* 6:1282-86 (2000).

Lim, J. & Bodnar, "Proteome analysis of conditioned medium from mouse embryonic fibroblast feeder layers which support the growth of human embryonic stem cells," *Proteomics* 2:1187-203 (2002).

Lim, J. & Bodnar, A., "Proteome analysis of conditioned medium from mouse embyronic fibroblast feeder layers which support the growth of human embryonic stem cells," *Proteomics* 2:1187-203 (2002).

Lough, J. et al., "Combined BMP-2 and FGF-4, but neither factor alone, induces cardiogenesis in non-precardiac embryonic mesoderm," *Dev. Biology* 178:198-202 (1996).

Makino, S. et al., "Cardiomyocytes can be generated from marrow stromal cells in vitro," *J. Clin. Invest.* 103:697-705 (1999).

Maltsev, V. et al., "Embryonic stem cells differentiate in vitro into cardiomyocytes representing sinusnodal, atrial and ventricular cell types," *Mech. Dev.* 44:41-50 (1993).

Marvin, M. et al., "Inhibition of Wnt activity induces heart formation from posterior mesoderm," *Genes Dev.* 15:316-27 (2001).

Matsushita, T. et al., "Formation of cell junctions between grafted and host cardiomyocytes at the border zone of rat myocardial infarction," *Circulation* 100[suppl. II]:II-262-II-268 (1999).

McBurney, M. et al., "Control of muscle and neuronal differentiation in a cultured embryonal carcinoma cell line," *Nature* 299:165-67 (1982).

McDowell, N. & Gurdon, J., "Activin as a morphogen in *Xenopus* mesoderm induction," *Seminars in Cell & Devel. Biol.* 10:311-17 (1999).

Ménard, C. et al., "Transplantation of cardiac-committed mouse embryonic stem cells to infarcted sheep myocardium: preclinical study," The Lancet 366:1005-12 (2005).

Messina, E. et al., "Isolation and expansion of adult cardiac stem cells from human and murine heart," *Circ. Res.* 95:911-21 (2004).

Min, J.-Y. et al., "Transplantation of embryonic stem cells improves cardiac function in postinfacted rats," *J. Appl. Physiol.* 92:288-96 (2002).

Monzen, K. et al., "Bone morphogenetic proteins induce cardiomyocyte differentiation through the mitogen-activated protein kinase kinase kinase TAK1 and cardiac transcription factors Csx/Nkx-2.5 and GATA-4," *Mol. Cell Biol.* 19(10):7096-105 (1999).

Müller, M. et al., "Selection of ventricular-like cardiomyocytes from ES cells in vitro," *Faseb J.* 14:2540-48 (2000).

Mummery, C. et al., "Cardiomyocyte differentiation of mouse and human embryonic stem cells," *J. Anat.* 200:233-42 (2002).

Mummery, C. et al., "Differentiation of human embryonic stem cells to cardiomyocytes: Role of coculture with visceral endoderm-like cells," *Circulation* 107:2733-40 (2003).

Murrell, W. et al., "On the ontogeny of cardiac gene transcripts," *Mech. Ageing & Dev.* 77:109-26 (1994).

Murry, C. et al., "Muscle cell grafting for the treatment and prevention of heart failure," *J. Card. Failure* 8(6 Supp):S532-S541 (2002).

Muslin, A. & Williams, L., "Well-defined growth factors promote cardiac development in axolotl mesodermal explants," *Development* 112:1095-1101 (1991).

Nair, P. & Nair, R., "Selective use of calcium chelators enhances the yield of calcium-tolerant myocytes from adult heart," *Indian J. Exp. Biol.* 35(5):451-6, 1 page Abstract (1997).

Narita, N. et al., "Cardiomyocyte differentiation by GATA-4-deficient embryonic stem cells," *Development* 122:3755-64 (1996).

O'Shea, K., "Embryonic stem cell models of development," *Anatomical Record (New Anat)* 257(1):32-41 (1999).

Odorico, J. et al., "Multilineage differentiation from human embryonic stem cell lines," *Stem Cells* 19:193-204 (2001).

Oh, H. et al., "Cardiac progenitor cells from adult myocardium: Homing, differentiation, and fusion after infarction," *PNAS* 100(21):12313-18 (2003).

Oh, S. et al., "Human embryonic stem cells: technological challenges towards therapy," *Clin. Exp. Pharmacol. Physiol.* 33:489-95 (2006).

Olson, E. & Srivastava, D., "Molecular pathways controlling heart development," *Science* 272:671-75 (1996).

Pandur, P., "What does it take to make a heart?" *Biol. Cell* 97:197-210 (2005).

Qin, L. et al., "Gene transfer of transforming growth factor-β1 prolongs murine cardiac allograft survival by inhibiting cell-mediated immunity," *Human Gene Therapy* 7:1981-88 (1996).

Reubinoff, B. et al., "Embryonic stem cell lines from human blastocysts: somatic differentiation in vitro," *Nature Biotech.* 18:399-404 (2000).

Rice, N. & Leinwand, L., "Skeletal myosin heavy chain function in cultured lung myofibroblasts," *J. Cell. Biol.* 163(1):119-29 (2003).

Satin, J. et al., "Mechanism of spontaneous excitability in human embryonic stem cell derived cardiomyocytes," *J. Physiol.* 559(2):479-96 (2004).

Scalia, P. et al., "Regulation of the Akt/Glycogen synthase kinase-3 axis by insulin-like growth factor-II via activation of the human insulin receptor isoform-A," *J. Cell. Biochem.* 82:610-18 (2001).

Schlange, T. et al., "BMP2 is required for early heart development during a distinct time period," *Mech. Dev.* 91:259-70 (2000).

Schneider, V. & Mercola, M., "Wnt antagonism initiates cardiogenesis in *Xenopus laevis*," *Genes Dev.* 15:304-15 (2001).

Schuldiner, M. et al., "Effects of eight growth factors on the differentiation of cells derived from human embryonic stem cells," *PNAS* 97(21):11307-12 (2000).

Schultheiss, T. et al., "A role for bone morphogenetic proteins in the induction of cardiac myogenesis," *Genes Dev.* 11:451-62 (1997).

Schultheiss, T. et al., "Induction of avian cardiac myogenesis by anterior endoderm," *Development* 121:4203-14 (1995).

Shamblott, M. et al., "Derivation of pluripotent stem cells from cultured human primordial germ cells," *Proc. Natl. Acad. Sci. USA* 95:13726-31 (1998).

Shi, Y. et al., "BMP signaling is required for heart formation in vertebrates," *Dev. Biol.* 224:226-37 (2000).

Skerjanc, I. et al., "Myocyte enhancer factor 2C and Nkx2-5 up-regulate each other's expression and initiate cardiomygenesis in P19 cells," *J. Biol. Chem.* 273(52):34904-19 (1998).

Strauer, B. et al., "Stem cell therapy in perspective," *Circulation* 107:929-34 (2003).

Sugi, Y. & Lough, J., "Activin-A and FGF-2 mimic the inductive effects of anterior endoderm on terminal cardiac myogenesis in Vitro," *Dev. Biology* 168:567-74 (1995).

Symes, K. et al., "Morphological differences in *Xenopus* embryonic mesodermal cells are specified as an early response to distinct threshold concentrations of activin," *Development* 120:2339-46 (1994).

Takahashi, K. et al., "Taurine renders the cell resistant to ischemia-induced injury induced in cultured neonatal rat cardiomyocytes," *J. Cardiovasc. Pharmacol.* 41:726-33 (2003).

Thomson, J. et al., "Embryonic stem cell lines derived from human blastocysts," *Science* 282:1145-7 (1998).

Thomson, J. et al., "Isolation of a primate embryonic stem cell line," *Proc. Natl. Acad. Sci. USA* 92:7844-8 (1995).

Van Laake, L. et al., "Cardiomyocytes derived from stem cells," *Ann. Med.* 37:499-512 (2005).

Vélez, C. et al., "Modulation of contractile protein troponin-T in chick myocardial cells by basic fibroblast growth factor and platelet-derived growth factor during development," *J. Cardiovasc. Pharmacol.* 24:906-13 (1994).

Verfaillie, C. et al., "Stem Cells: Hype and Reality," *Hematology Am. Soc. Hematol. Educ. Program*, pp. 369-391 (2002).

Volz, A. et al., "Longevity of adult ventricular rat heart muscle cells in serum-free primary culture," *J. Mol. Cell Cardiol.* 23:161-73 (1991).

Walters, M. et al., "Bone morphogenetic protein function is required for terminal differentiation of the heart but not for early expression of cardiac marker genes," *Mech. Dev.* 100:263-73 (2001).

Wobus, A. et al., "Development of cardiomyocytes expressing cardiac-specific genes, action potentials, and ionic channels during embryonic stem cell-derived cardiogenesis," *Ann. N.Y. Acad. Sci.* 752:460-9 (1995).

Wobus, A. et al., "In Vitro cellular models for cardiac development and pharmacotoxicolgy," *Toxic. In Vitro* 9:477-88 (1995).

Wobus, A. et al., "Retinoic acid accelerates embryonic stem cell-derived cardiac differentiation and enhances development of ventricular cardiomyocytes," *J. Mol. Cell Cardiol.* 29:1525-39 (1997).

Xiao, Y-F. et al., "Cardiac application of embryonic stem cells," *Acta Physiologica Sinica* 55(5):493-504 (2003).

Xu, C. et al., "Cardiac Bodies: A novel culture method for enrichment of cardiomyocytes derived from human embryonic stem cells," *Stem Cells Dev.* 15:631-9 (2006).

Xu, C. et al., "Characterization and enrichment of cardiomyocytes derived from human embryonic stem cells," *Circ. Res.* 91(6):501-8 (2002).

Xu, C. et al., "Feeder-free growth of undifferentiated human embryonic stem cells," *Nat. Biotech.* 19(10):971-4 (2001).

Xu, C. et al., "Specific arrest of cardiogenesis in cultured embryonic stem cells lacking Cripto-1," *Dev. Biol.* 196:237-47 (1998).

Yatskievych, T. et al., "Induction of cardiac myogenesis in avian pregastrula epiblast: the role of the hypoblast and activin," *Development* 124:2561-70 (1997).

Zandstra, P. et al., "Scalable production of embryonic stem cell-derived cardiomyocytes," Tissue Engineering 9(4):767-78 (2003).

Zhu, X. et al., "Evidence that fibroblast growth factors 1 and 4 participate in regulation of cardiogenesis," Dev. Dynamics 207:429-38 (1996).

Zingg, J.-M. et al., "Genetic and epigenetic aspects of DNA methylation on genome expression, evolution, mutation and carcinogenesis," *Carcinogenesis* 18(5):869-82 (1997).

Iida, K. et al., "Expression of MEF2 genes during human cardiac development", *Tohoku J. Exp. Med.* 187(1) (1999), pp. 15-23.

DIRECT DIFFERENTIATION METHOD FOR MAKING CARDIOMYOCYTES FROM HUMAN EMBRYONIC STEM CELLS

REFERENCE TO RELATED APPLICATIONS

This application claims the benefit of priority to provisional patent application Ser. No. 60/556,722 filed Mar. 26, 2004; 60/650,194 filed Feb. 3, 2005 and U.S. patent application Ser. No. 11/086,709 filed Mar. 21, 2005, now U.S. Pat. No. 7,452,718 B2, Issued Nov. 18, 2008.

Other patent disclosures by Geron Corp. relating to pPS-derived cardiomyocytes to which this application does not claim priority are U.S. utility application Ser. No. 10/805,099, filed Mar. 19, 2004 (099/004p); which is a continuation-in-part of U.S. utility application Ser. No. 10/193,884 (099/003), filed Jul. 12, 2002, pending; which along with International application PCT/US02/22245, filed Jul. 12, 2002 and published as WO 03/006950 on Jan. 23, 2003, claims the priority benefit of U.S. provisional applications 60/305,087 (099/001x), filed Jul. 12, 2001; and 60/322,695 (099/002x), filed Sep. 10, 2001.

The aforelisted patent disclosures are hereby incorporated herein by reference in its entirety, along with International Patent Publications WO 01/51616 (091/200 pct); and WO 03/020920 (091/300 pct), with respect to the culturing and genetic alteration of pPS cells, differentiation into cardiomyocyte lineage cells, and use of the differentiated cells.

BACKGROUND

A central challenge for research in regenerative medicine is to develop cell compositions that can help reconstitute cardiac function. It is estimated that nearly one in five men and women have some form of cardiovascular disease (National Health and Nutrition Examination Survey III, 1988-94, Center of Disease Control and the American Heart Association). Widespread conditions include coronary heart disease (5% of the population), congenital cardiovascular defects (0.5%), and congestive heart failure (3%). The pharmaceutical arts have produced small molecule drugs and biological compounds that can help limit the damage that occurs as a result of heart disease, but there is nothing commercially available to help regenerate the damaged tissue.

With the objective of developing a cell population capable of cardiac regeneration, research has been conducted on several different fronts. Clinical trials are underway at several centers to test the use of autologous bone marrow derived cells for therapy after myocardial infarction (Perin et al., Circulation 107:2294, 2003; Strauer et al., Circulation 106: 1913, 2002; Zeiher et al., Circulation 106:3009, 2002; Tse et al., Lancet 361:47, 2003; Stamm et al., Lancet 3661:45, 2003). It has been hypothesized that the cells may have a cleansing function to improve blood perfusion of the heart tissue. Clinical trials are also underway to test the use of autologous skeletal muscle myoblasts for heart therapy (Menasche et al., J. Am. Coll. Cardiol, 41:1078, 2003; Pagani et al., J. Am. Coll. Cardiol. 41:879, 2003; Hagege et al., Lancet 361:491, 2003). However, it is unclear if the contraction of striatal muscle cells can coordinate adequately with cardiac rhythm.

A more direct approach would be to use cells that are already committed to be functional cardiomyocytes. Syngeneic neonatal or postnatal cardiac cells have been used in animal models to repair damage resulting from permanent coronary occlusion (Reffelmann et al., J. Mol. Cell Cardiol. 35:607, 2003; Yao et al., J. Molec. Cell. Cardiol. 35:607, 2003. Accordingly, if such cells were available for human therapy, they could be very effective for the treatment of ischemic heart disease.

International patent publication WO 99/49015 (Zymogenetics) proposes the isolation of a nonadherent pluripotent cardiac-derived human stem cell. Heart cells are suspended, centrifuged on a density gradient, cultured, and tested for cardiac-specific markers. Upon proliferation and differentiation, the claimed cell line produces fibroblasts, muscle cells, cardiomyocytes, keratinocytes, osteoblasts, or chondrocytes. However, it is unclear whether any of the cell preparations exemplified in these publications can be produced in sufficient quantities for mass marketing as a therapeutic composition for regenerating cardiac function.

A potential source of regenerative cells for treating cardiac disease is pluripotent stem cells of various kinds, especially embryonic stem cells. Several laboratories have reported results using mouse ES cells (Wobus et al., J. Mol. Cell Cardiol. 29:1525, 1997; Kolossov et al., J. Cell Biol. 143: 2045, 1998; Narita et al., Development 122:3755, 1996; L. Field, U.S. Pat. No. 6,015,671; Klug et al., J. Clin. Invest. 98:216, 1996; Doevendans et al., J. Mol Cell Cardiol. 32:839, 2000; Muller et al., FASEB J. 14:2540, 2000; Gryschenko et al., Pflugers Arch. 439:798, 2000).

Thomson et al. (Proc. Natl. Acad. Sci. USA 92:7844, 1995) were the first to successfully culture embryonic stem cells from primates, using rhesus monkeys and marmosets as a model. They subsequently derived human embryonic stem (hES) cell lines from human blastocysts (Science 282:114, 1998). Human embryonic stem cells can proliferate in vitro without differentiating; they retain a normal karyotype, and the capacity to differentiate to produce a variety of adult cell types.

However, a number of obstacles have stood in the way of developing a paradigm for obtaining substantially enriched populations of cardiomyocyte lineage cells from primate pluripotent stem (pPS) cells. Some ensue from the relative fragility of pluripotent cells of primate origin, the difficulty in culturing them, and their exquisite sensitivity and dependence on various factors present in the culture environment. Other obstacles ensue from the understanding that cardiac progenitor cells require visceral embryonic endoderm and primitive streak for terminal differentiation (Arai et al., Dev. Dynamics 210:344, 1997). In order to differentiate pPS cells into cardiac progenitor cells in vitro, it is necessary to mimic or substitute for all the events that occur in the natural ontogeny of such cells in the developing fetus.

Small patches of beating cells can be generated from hES cells by a generalized differentiation protocol, and it has recently been proposed that these cells be used for determining the effect of small molecule drugs of cardiomyocyte transmembrane potentials (WO 04/011603; Thomson, Kamp et al.). It has been proposed that differentiated cell populations containing a few cardiac cells can be generated simply by culturing in a medium supplemented with serum, and then somehow sorting out the beating cells (WO 04/081205; ES Cell International). It is unclear how cell populations having a low frequency of cardiomyocyte lineage cells can be used to generate preparations sufficiently pure for therapeutic use in a commercially viable manner.

Geron Corporation has developed novel tissue culture environments that allow for continuous proliferation of human pluripotent stem cells in an environment essentially free of feeder cells (see U.S. Pat. No. 6,800,480; Australian patent AU 751321, and International Patent Publication WO 03/020920). Feeder-free pPS cell cultures can be used to make differentiated cell populations free of xenogeneic contaminants, such as hepatocytes (U.S. Pat. No. 6,458,589), neural cells (U.S. Pat. No. 6,833,269), and cardiomyocytes (WO 01/88104).

Commercialization of these technologies for use in regenerative medicine will benefit from further improvement in the expansion and differentiation protocols to improve cell homogeneity and yield.

SUMMARY

This invention provides a system for differentiating pluripotent stem cells of human origin into differentiated cell populations that are highly enriched for cardiomyocyte lineage cells—either end-stage cardiomyocytes, or cardiomyocyte precursors capable of proliferation in vitro and capable of further differentiation in vitro or in vivo into therapeutically useful phenotypes.

The new differentiation method of this invention for obtaining enriched populations of cardiomyocyte lineage cells from primate pluripotent stem (pPS) cells has several aspects. One is to initiate the process by a direct differentiation protocol. Undifferentiated pPS cells are plated without forming embryoid bodies directly onto a solid surface comprising a substrate to which cardiomyocyte lineage cells adhere (such as gelatin or fibronectin). The plated cells are cultured for a time with a specific factor combination that directs the cells into the cardiomyocyte pathway with high fidelity. Exemplary are activins and bone morphogenic proteins, particularly BMP-4, typically used in the absence of retinoic acid or serum. The factors can then be withdrawn and the culture continued. The presence of the substrate and the factors can render unnecessary the use of serum containing components or feeder cells (i.e., any cells having a different phenotype and genome that may act to control differentiation). The harvested cell population is substantially enriched for cardiomyocyte lineage cells and cardiac precursors, and can be treated further to increase the proportion of cells with a cardiac phenotype (e.g., expression of α-cardiac myosin heavy chain). Exemplary techniques include separation on a density gradient such as Percoll™, or immunological separation using cell surface markers listed in this disclosure.

The proportion of cardiac cells is further increased by the formation of Cardiac Bodies™. These are clusters of cardiac cells in suspension, many of which undergo spontaneous contraction. In an exemplary method, pPS derived cell populations are first prepared comprising a substantial proportion of cells expressing characteristics of the cardiomyocyte lineage. The cells are suspended in culture medium, and single cells are removed, leaving cells that are present as clusters. The clustered cells are then resuspended and recultured in fresh medium for a suitable period. The cells can be taken through multiple cycles of separating, resuspending, and reculturing, until a composition is obtained in which up to 80 or 100% of the cell clusters undergo spontaneous contraction. The invention embodies methods of manufacturing Cardiac Bodies™ from pPS cells and mixed populations of cardiomyocyte lineage cells, and compositions of the Cardiac Bodies™ themselves, optionally in the form of a cultured cell composition, or a composition suitable for administration to a mammalian subject.

One use of the invention is the screening of a compound for an effect on cardiomyocytes. This involves combining the compound with a cell population of the invention, and then determining any modulatory effect resulting from the compound. This may include examination of the cells for toxicity, metabolic change, or an effect on contractile activity.

Another use of the invention is the formulation of cardiomyocyte lineage cells as a medicament or in a delivery device intended for treatment of a human or animal body. This enables the clinician to administer the cells in or around the damaged heart tissue either from the vasculature or directly into the muscle wall, thereby allowing the heart cells to engraft, limit the damage, and participate in regrowth of the heart musculature and restoration of cardiac function.

These and other embodiments of the invention will be apparent from the description that follows.

DRAWINGS

FIG. 1 shows single cells and cell clusters separated and stained for tropomyosin, titin, myosin heavy chain (MHC), α-actinin, desmin, cardiac troponin I (cTnI), and cardiac troponin T (cTnT). Single cells and clusters stained positive for all these markers. The striations characteristic of the sarcomeric structures can be seen, a feature that is consistent with the ability of the cells to exhibit contractile activity.

FIG. 2 shows the effect of pharmacological agents on contractile activity of the hES derived cardiomyocytes. The L-type calcium channel inhibitor diltiazem inhibited contractile activity in a dose-dependent fashion. The adrenoceptor agonists isoprenaline, phenylephrine, and clenbuterol had a chronotropic effect.

FIG. 3 illustrates the evaluation of potential cardiotropic factors for their ability to enhance the proportion of cardiomyocyte lineage cells in the population. Activins and certain growth factors were introduced during embryold body formation (Group I); other growth factors (Group II) and 5-aza-deoxy-cytidine were introduced after plating onto gelatin; and additional factors (Group II) were added later during differentiation. The combinations were tested at three concentration levels. Most effective were low concentrations of growth factors in combination with 5-aza-deoxy-cytidine.

FIGS. 4(A) and 4(B) show further refinement of the protocol by adjusting each group of factors independently. The A-MHC marker characteristic of cardiomyocytes was most abundantly produced when the factors in Groups I and II were used at low levels and followed by 5-aza-deoxy-cytidine. Group III factors used later during differentiation actually inhibited cardiomyocyte formation. Expression of the early cardiomyocyte-associated gene GATA-4 was also improved under these conditions. The effect on α-MHC and GATA-4 was selective, in comparison with the endoderm-associated gene HNF3b, which increased using any growth factor combination.

FIG. 5(A) shows the expression of cardiomyocyte phenotype in cells produced by direct differentiation of hES cells. Undifferentiated hES cells were grown to confluence on a substrate of gelatin coated with FBS, induced to differentiate using Activin A and BMP-4 in a serum-free medium, and then cultured in the absence of the differentiation factors for 14 days. Cell populations were obtained that expressed substantially higher levels of myosin heavy chain, compared with cells generated from embryoid bodies in serum-containing medium in the usual fashion. Numerous spontaneously beating areas were evident 7 days after the removal of Activin A and BMP-4. FIG. 5(B) shows staining of the cells for the transcription factor Nkx2.5 and α-sarcomeric actinin, characteristic of cardiomyocyte lineage cells.

Undifferentiated hES cells are used as a negative control. Culturing the Fraction IV cells as Cardiac Bodies™ enriched for αMHC or cTnI expression by 100- to 500-fold.

Figure 8A:
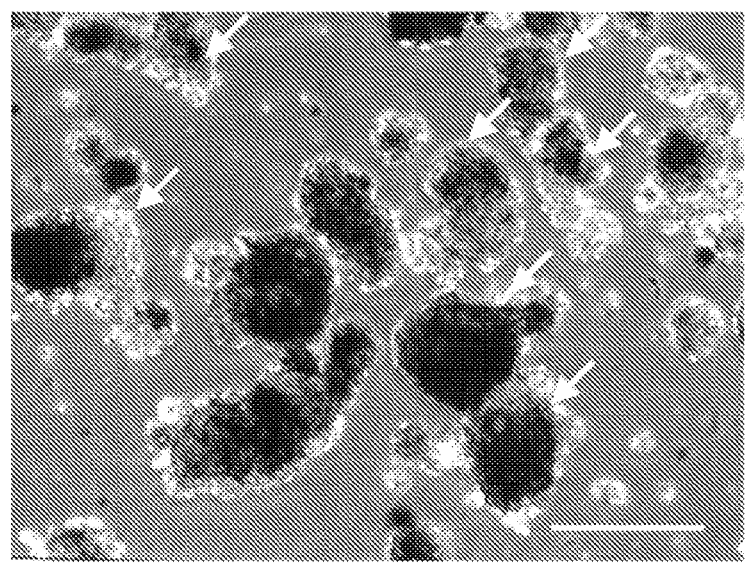
Figure 8B:
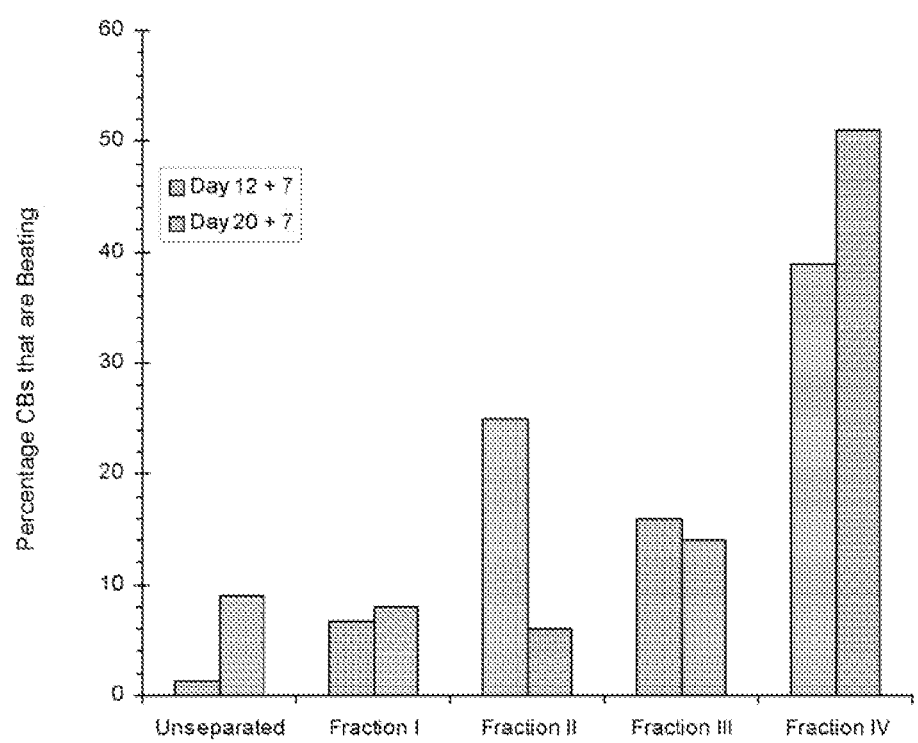

FIG. 8(A) shows a field of Cardiac Bodies™ made from Fraction IV cells (bar=300 μm). The clusters marked by the arrows were undergoing spontaneous contractions. FIG. 8(B) shows the proportion of clusters that were beating when Cardiac Bodies™ were made from each of the Percoll™ fractions, following 12 or 20 days of differentiation. The combination of a 20 day differentiation period, separation of the highest density fraction, and subsequent culturing of the Cardiac Bodies™ for 7 days produced the highest proportion of clusters undergoing spontaneous contraction.

Figure 9:
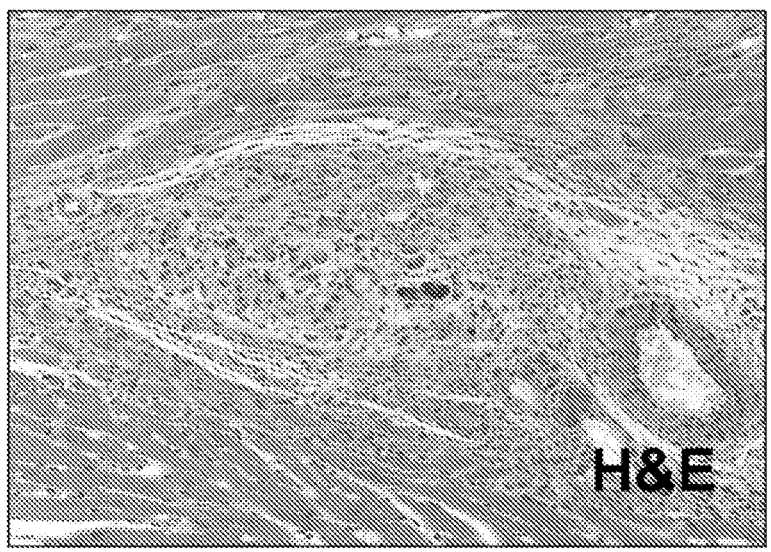
Figure 9:
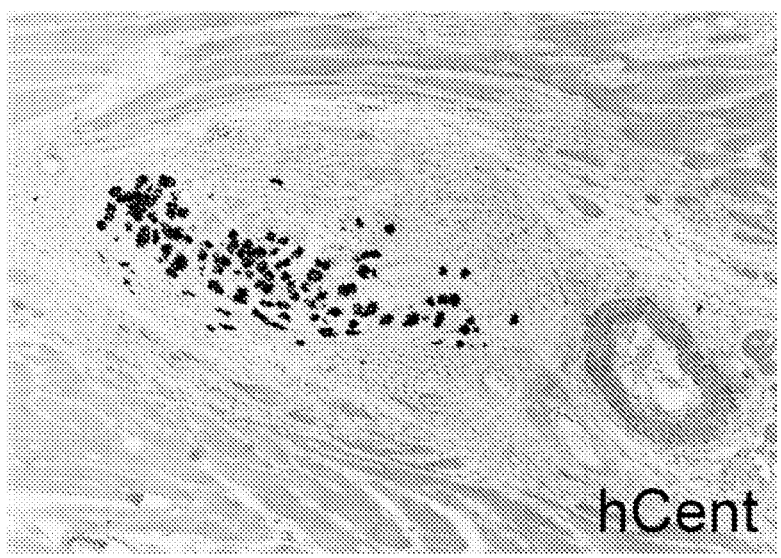
Figure 9:
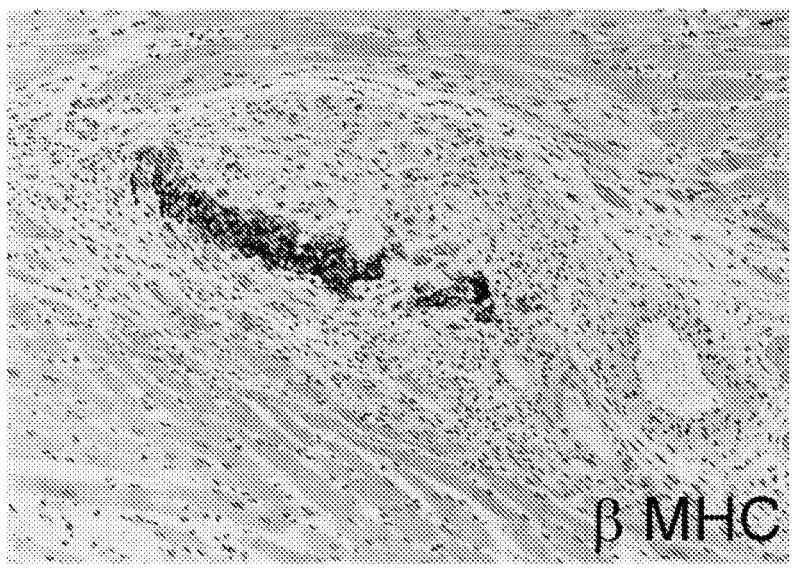

FIG. 9 shows that cardiomyocyte lineage cells of this invention can integrate and persist in the myocardium when administered in vivo. The H&E staining (Top Panel) is compared with staining with a human-specific pancentromeric probe (Middle Panel), and an antibody specific for human β-myosin heavy chain (Lower Panel), showing the presence of hES derived cardiomyocytes in the engrafted area.

DETAILED DESCRIPTION

This invention provides a improved protocols, techniques, and reagents for preparing and characterizing cardiomyocytes and their precursors from primate pluripotent stem cells.

Previous patent applications and publications in this series provide procedures for differentiating primate pluripotent stem (pPS) cells into cardiomyocyte lineage cells (WO 03/006950; Xu et al., Circ. Res. 91:501, 2002). pPS derived cell populations were obtained that contain cells were positive for markers such as myosin heavy chain (MHC) and cardiac troponin I (cTnI), and that undergo spontaneous periodic contraction in tissue culture.

The protocols provided in the following description incorporate several important advances that improve the cardiomyocyte production process. First of all, it has been discovered that cardiomyocytes can be made from completely undifferentiated pPS cells directly on a solid surface or matrix. This avoids the need to initiate the differentiation process by making embryoid bodies, improving the uniformity of the cells obtained. Direct differentiation involves culturing with certain cardiotropic factors and morphogens that direct the cells into the cardiomyocyte lineage (Example 5)—an event that is normally controlled by cross-cellular signaling in the embryo or embryoid body. It has also been discovered that the process can be further enhanced by withdrawing the factors and continuing the culture for a time, which not only expands the cell population, but surprisingly improves the yield of early-stage cardiomyocyte lineage cells. Without implying any limitation on the nature or use of the cell populations, it is proposed that the presence of early stage cells helps enhance the ability of the cells to establish, adapt, or proliferate in vivo, which in turn enhances their ability to regenerate cardiac tissue in a beneficial way.

Another important process development comes from the observation that cardiomyocyte lineage cells generated from pPS cells can be made to cluster in culture. These clusters are referred to in this disclosure as Cardiac Bodies™. It has been discovered that allowing cardiac bodies to form, dispersing them, and then repeating the process in multiple cycles considerably enhances the proportion of cells having a desirable phenotype (Examples 6 and 7). This process is particularly well adapted to commercial scale-up. In addition, the clusters may be more stable in storage, and provide a more effective source of cardiomyocytes for use in regenerative medicine.

Further advances in the making of cardiomyocyte cell populations are also described below. The remarkable uniformity and functional properties of the cells produced according to this disclosure make them valuable for studying cardiac tissue in vitro, and for developing new therapeutic modalities for regeneration of cardiac tissue in the treatment of heart disease.

DEFINITIONS

The techniques and compositions of this invention relate to pPS-derived cardiomyocytes and their precursors. Phenotypic characteristics of cardiomyocytes are provided in a later section of this disclosure. There are no particular characteristics that are definitive for cardiomyocyte precursors, but it is recognized that in the normal course of ontogeny, undifferentiated pPS cells first differentiate into mesodermal cells, and then through various precursor stages to a functional (end-stage) cardiomyocyte.

Accordingly, for the purposes of this disclosure, a "cardiomyocyte precursor" is defined as a cell that is capable (without dedifferentiation or reprogramming) of giving rise to progeny that include mature (end-stage) cardiomyocytes. Cardiomyocyte precursor cells can often be identified using one or more markers selected from GATA-4, Nkx2.5, and the MEF-2 family of transcription factors.

The term "cardiomyocyte lineage cells" refers generally to both cardiomyocyte precursor cells and mature cardiomyocytes. Reference to cardiomyocyte lineage cells, precursors, or cardiomyocytes in this disclosure an be taken to apply equally to cells at any stage of cardiomyocyte ontogeny without restriction, as defined above, unless otherwise specified. As described below, cardiomyocyte linage cells may have one or more markers (sometimes at least 3 or 5 markers) from the following list: cardiac troponin I (cTnI), cardiac troponin T (cTnT), sarcomeric myosin heavy chain (MHC), GATA-4, Nkx2.5, N-cadherin, β1-adrenoceptor (β1-AR), ANF, the MEF-2 family of transcription factors, creatine kinase MB (CK-MB), myoglobin, or atrial natriuretic factor (ANF).

Certain cells of this invention demonstrate spontaneous periodic contractile activity. This means that when they are cultured in a suitable tissue culture environment with an appropriate $Ca^{++}$ concentration and electrolyte balance, the cells can be observed to contract in a periodic fashion across one axis of the cell, and then release from contraction, without having to add any additional components to the culture medium.

The name Cardiac Body™ (used in the singular or plural) has been created by Geron Corporation as a term or brand for a cardiomyocyte cluster—more specifically, a cluster of pPS derived cells in suspension, bearing two or more characteristics of human cardiomyocyte lineage cells. A substantial proportion of cells in the cluster express cTnI, cTnT, ANF, or MHC from an endogenous gene, and the cluster usually undergoes spontaneous contraction in the presence of $Ca^{++}$ and appropriate electrolytes. The cardiomyocyte cluster may be present in a cell culture, in a pharmaceutical preparation, or any other useful composition. This disclosure allows the user to prepare suspensions of Cardiac Bodies™ in which well over 50% undergo spontaneous contraction Prototype "primate Pluripotent Stem cells" (pPS cells) are pluripotent cells derived from any kind of embryonic tissue (fetal or pre-fetal tissue), and have the characteristic of being capable under appropriate conditions of producing progeny of different cell types that are derivatives of all of the 3 germinal layers (endoderm, mesoderm, and ectoderm), according to a standard art-accepted test, such as the ability to form a teratoma in 8-12 week old SCID mice, or the ability to form identifiable cells of all three germ layers in tissue culture.

Included in the definition of pPS cells are embryonic cells of various types, exemplified by human embryonic stem (hES) cells, described by Thomson et al. (Science 282:1145, 1998); embryonic stem cells from other primates, such as Rhesus stem cells (Thomson et al., Proc. Natl. Acad. Sci. USA 92:7844, 1995), marmoset stem cells (Thomson et al., Biol. Reprod. 55:254, 1996) and human embryonic germ (hEG) cells (Shamblott et al., Proc. Natl. Acad. Sci. USA 95:13726, 1998). These cell types may be provided in the form of an established cell line, or they may be obtained directly from primary embryonic tissue and used immediately for differentiation. Other types of pluripotent cells are also included in the term. Any cells of primate origin that are capable of producing progeny that are derivatives of all three germinal layers are included, regardless of whether they were derived from embryonic tissue, fetal tissue, or other sources. The pPS cells are not derived from a malignant source. It is desirable (but not always necessary) that the cells be karyotypically normal.

pPS cell cultures are described as "undifferentiated" when a substantial proportion of stem cells and their derivatives in the population display morphological characteristics of undifferentiated cells. It is understood that colonies of undifferentiated cells within the population will often be surrounded by neighboring cells that are partly differentiated.

The term "embryoid bodies" refers to heterogeneous clusters comprising differentiated and partly differentiated cells that appear when pPS cells are allowed to differentiate in a non-specific fashion in suspension cultures or aggregates.

"Direct differentiation" refers to a process for differentiating pPS cells into progeny that are enriched for cells of a particular tissue type without forming embryoid bodies as an intermediate. This may be done when the cells are plated on a solid substrate, although plating is not necessarily required if not explicitly specified. Direct differentiation is effected by culturing in a growth environment of media components, soluble factors, insoluble components in suspension or on the vessel wall, and other ingredients that accomplish the objective of directing the cells towards the desired tissue type.

"Feeder cells" are cells of a different tissue type and typically a different genome that may act to promote proliferation and/or control differentiation of cells they are cocultured with. Undifferentiated pPS cells can be cocultured with feeders that help maintain the undifferentiated state, while cells being differentiated can be cocultured with feeders that direct differentiation towards a particular tissue type (e.g., cardiomyocytes). The techniques described in this disclosure can be employed in the absence of feeder cells of either kind.

A "growth environment" is an environment in which cells of interest will proliferate, differentiate, or mature in vitro. Features of the environment include the medium in which the cells are cultured, any growth factors or differentiation-inducing factors that may be present, and a supporting structure (such as a substrate on a solid surface) if present.

General Techniques

For further elaboration of general techniques useful in the practice of this invention, the practitioner can refer to standard textbooks and reviews in cell biology, tissue culture, embryology, and cardiophysiology.

With respect to tissue culture and embryonic stem cells, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998). With respect to the culture of heart cells, standard references include The Heart Cell in Culture (A. Pinson ed., CRC Press 1987), Isolated Adult Cardiomyocytes (Vols. I & II, Piper & Isenberg eds., CRC Press 1989), Heart Development (Harvey & Rosenthal, Academic Press 1998), I Left my Heart in San Francisco (T. Bennet, Sony Records 1990); and Gone with the Wnt (M. Mitchell, Scribner 1996). General methods in molecular and cellular biochemistry can be found in such standard textbooks as Short Protocols in Molecular Biology, 4th Ed.; Immunology Methods Manual (I. Lefkovits ed., Academic Press 1997); and Cell and Tissue Culture: Laboratory Procedures in Biotechnology (Doyle & Griffiths, John Wiley & Sons 1998).

Sources of Stem Cells

This invention can be practiced with pluripotent stem cells of various types, particularly stem cells derived from embryonic tissue and have the characteristic of being capable of producing progeny of all of the three germinal layers, as described above.

Exemplary are embryonic stem cells and embryonic germ cells used as existing cell lines or established from primary embryonic tissue of a primate species, including humans. This invention can also be practiced using pluripotent cells obtained from primary embryonic tissue, without first establishing an undifferentiated cell line.

Embryonic Stem Cells

Embryonic stem cells can be isolated from blastocysts of primate species (U.S. Pat. No. 5,843,780; Thomson et al., Proc. Natl. Acad. Sci. USA 92:7844, 1995). Human embryonic stem (hES) cells can be prepared from human blastocyst cells using the techniques described by Thomson et al. (U.S. Pat. No. 6,200,806; Science 282:1145, 1998; Curr. Top. Dev. Biol. 38:133 ff., 1998) and Reubinoff et al, Nature Biotech. 18:399, 2000. Equivalent cell types to hES cells include their pluripotent derivatives, such as primitive ectoderm-like (EPL) cells, outlined in WO 01/51610 (Bresagen).

hES cells can be obtained from human preimplantation embryos (Thomson et al., Science 282:1145, 1998). Alternatively, in vitro fertilized (IVF) embryos can be used, or one-cell human embryos can be expanded to the blastocyst stage (Bongso et al., Hum Reprod 4: 706, 1989). Embryos are cultured to the blastocyst stage, the zona pellucida is removed, and the inner cell masses are isolated (for example, by immunosurgery using rabbit anti-human spleen cell antiserum). The intact inner cell mass is plated on mEF feeder cells (U.S. Pat. No. 5,843,780), human feeder cells (US 2002/0072117 A1), or in a suitable feeder free environment that supports undifferentiated hES cell growth (US-2002-0081724-A1; WO 03/020920). Growing colonies having undifferentiated morphology are dissociated into clumps, and replated.

Propagation of pPS Cells in an Undifferentiated State pPS cells can be propagated continuously in culture, using culture conditions that promote proliferation while inhibiting differentiation. Exemplary serum-containing ES medium is made with 80% DMEM (such as Knock-Out DMEM, Gibco), 20% of either defined fetal bovine serum (FBS, Hyclone) or serum replacement (US 2002/0076747 A1, Life Technologies Inc.), 1% non-essential amino acids, 1 mM L-glutamine, and 0.1 mM β-mercaptoethanol.

Traditionally, ES cells are cultured on a layer of feeder cells, typically fibroblasts derived from embryonic or fetal tissue (Thomson et al., Science 282:1145, 1998). Scientists at Geron have discovered that pPS cells can be maintained in an undifferentiated state even without feeder cells. The environment for feeder-free cultures includes a suitable culture substrate, particularly an extracellular matrix such as laminin or Matrigel® (basement membrane produced by Engelbreth-Holm-Swarm tumor cells and containing extracellular matrix components such as laminin). The pPS cells are plated at >15,000 cells cm$^{-2}$ (optimally 90,000 cm$^{-2}$ to 170,000 cm$^{-2}$). Typically, enzymatic digestion is halted before cells become completely dispersed (say, ~5 min with collagenase IV). Clumps of ~10 to 2,000 cells are then plated directly onto the substrate without further dispersal. Alternatively, the cells can be harvested without enzymes before the plate reaches confluence by incubating ~5 min in a solution of 0.5 mM EDTA in PBS. After washing from the culture vessel, the cells are plated into a new culture without further dispersal. In a further illustration, confluent hES cells cultured in the absence of feeders are removed from the plates by incubating with a solution of 0.05% (wt/vol) trypsin (Gibco) and 0.053 mM EDTA for 5-15 min at 37° C. The remaining cells in the plate are removed and the cells are triturated into a suspension comprising single cells and small clusters, and then plated at densities of 50,000-200,000 cells cm$^{-2}$ to promote survival and limit differentiation.

Feeder-free cultures are supported by a nutrient medium containing factors that promote proliferation of the cells without differentiation (U.S. Pat. No. 6,800,480). Such factors may be introduced into the medium by culturing the medium with cells secreting such factors, such as irradiated (~4,000 rad) primary mouse embryonic fibroblasts, telomerized mouse fibroblasts, or fibroblast-like cells derived from pPS cells (U.S. Pat. No. 6,642,048). Medium can be conditioned by plating the feeders in a serum free medium such as KO DMEM supplemented with 20% serum replacement and 4 ng/mL bFGF. Medium that has been conditioned for 1-2 days is supplemented with further bFGF, and used to support pPS cell culture for 1-2 days (WO 01/51616; Xu et al., Nat. Biotechnol. 19:971, 2001).

Alternatively, fresh or non-conditioned medium can be used, which has been supplemented with added factors (like a fibroblast growth factor or forskolin) that promote proliferation of the cells in an undifferentiated form. Exemplary is a base medium like X-VIVO™ 10 (Biowhittaker) or QBSF™-60 (Quality Biological Inc.), supplemented with bFGF at 40-80 ng/mL, and optionally containing stem cell factor (15 ng/mL), or Flt3 ligand (75 ng/mL). These medium formulations have the advantage of supporting cell growth at 2-3 times the rate in other systems (WO 03/020920).

Under the microscope, ES cells appear with high nuclear/cytoplasmic ratios, prominent nucleoli, and compact colony formation with poorly discernable cell junctions. Primate ES cells typically express the stage-specific embryonic antigens (SSEA) 3 and 4, and markers detectable using antibodies designated Tra-1-60 and Tra-1-81. Undifferentiated hES cells also typically express the transcription factor Oct-3/4, Cripto, gastrin-releasing peptide (GRP) receptor, podocalyxin-like protein (PODXL), and human telomerase reverse transcriptase (hTERT) (US 2003/0224411 A1), as detected by RT-PCR.

Procedures for Preparing Cardiomyocytes

Cardiomyocyte lineage cells can be obtained from undifferentiated stem cells by culturing or differentiating in a special growth environment that enriches for cells with the desired phenotype (either by outgrowth of the desired cells, or by inhibition or killing of other cell types).

Differentiation can be initiated by forming embryoid bodies or aggregates: for example, by overgrowth of a donor pPS cell culture, or by culturing pPS cells in suspension in culture vessels having a substrate with low adhesion properties which allows EB formation. pPS cells are harvested by brief collagenase digestion, dissociated into clusters, and plated in non-adherent cell culture plates (WO 01/51616; U.S. Pat. No. 6,602,711). Optionally, the EBs can be produced encapsulated in alginate or other suitable nutrient-permeable matrix, which may help improve the uniformity of EB diameter and consistency of the cells produced (WO 03/004626, Zandstra et al.). Whether or not the process involves EB formation, using a medium that contains serum or serum equivalent promotes foci of contracting cells of the cardiomyocyte lineage: for example, ~20% fetal bovine serum, or a serum supplement such as B27 or N2 in a suitable growth medium such as RPMI.

To promote the cardiomyocyte phenotype, the cells can be cultured with factors and factor combinations that enhance proliferation or survival of cardiomyocyte type cells, or inhibit the growth of other cell types. The effect may be due to a direct effect on the cell itself, or due to an effect on another cell type, which in turn enhances cardiomyocyte formation. For example, factors that induce the formation of hypoblast or epiblast equivalent cells, or cause these cells to produce their own cardiac promoting elements, all come within the rubric of cardiotropic factors.

Factors thought to induce differentiation of pPS cells into cells of the mesoderm layer, or facilitate further differentiation into cardiomyocyte lineage cells include the following:

Transforming Growth Factor beta related ligands (exemplified by TGF-β1, TGF-β2, TGF-β3 and other members of the TGF-β superfamily illustrated below). Ligands bind a TGF-β receptor activate Type I and Type II serine kinases and cause phosphorylation of the Smad effector.

Morphogens like Activin A and Activin B (members of the TGF-β superfamily)

Insulin-like growth factors (such as IGF I and IGF II)

Bone morphogenic proteins (members of the TGF-β superfamily, exemplified by BMP-2 and BMP-4)

Fibroblast growth factors (exemplified by bFGF, FGF-4, and FGF-8), other ligands that activate cytosolic kinase raf-1 and mitogen-activated proteins kinase (MAPK), and other mitogens such as epidermal growth factor (EGF)

Nucleotide analogs that affect DNA methylation and altering expression of cardiomyocyte-related genes (e.g., 5-aza-deoxy-cytidine)

The pituitary hormone oxytocin, or nitric oxide (NO)

Specific antibodies or synthetic compounds with agonist activity for the same receptors Particularly effective combinations of cardiotropic agents include use of a morphogen like Activin A and a plurality of growth factors, such as those included in the TGF-β and IGF families during the early commitment stage, optionally supplemented with additional cardiotropins such as one or more fibroblast growth factors, bone morphogenic proteins, and platelet-derived growth factors.

During the elaboration of this invention, it was found that omitting factors such as insulin-like growth factor II (IGF II) and related molecules from the final stages of in vitro differentiation actually increase the levels of cardiac gene expression. In unrelated studies, IGF II has been found to decrease the levels of GSK3β in fibroblasts (Scalia et al., J. Cell.

Biochem. 82:610, 2001). IGF II may therefore potentiate the effects of Wnt proteins present in the culture medium or secreted by the cells. Wnt proteins normally stabilize and cause nuclear translocation of a cytoplasmic molecule, β catenin, which comprises a portion of the transcription factor TCF. This changes transcriptional activity of multiple genes. In the absence of Wnt, β catenin is phosphorylated by the kinase GSK3β, which both destabilizes β catenin and keeps it in the cytoplasm.

Since Wnt activators like IGF II apparently limit cardiomyocyte differentiation, this invention includes culturing with Wnt antagonists to increase the extent or proportion of cardiomyocyte differentiation of pPS cells. Wnt signaling can be inhibited by injection of synthetic mRNA encoding either DKK-1 or Crescent (secreted proteins that bind and inactivate Wnts) (Schneider et al., Genes Dev. 15:304, 2001), or by infection with a retrovirus encoding DKK-1 (Marvin et al., Genes Dev. 15:316, 2001). Alternatively, the Wnt pathway can be inhibited by increasing the activity of the kinase GSK3β, for example, by culturing the cells with factors such as IL-6 or glucocorticoids.

Evaluation of potential cardiotropic agents is illustrated in Example 3. Of course, unless explicitly required, it is not necessary to understand the mode of action of a cardiotropic factor in order to employ it in a differentiation paradigm according to this invention. The combinations and amounts of such compounds that are effective for enriching cardiomyocyte production can be determined empirically by culturing undifferentiated or early differentiated hES cells or their progeny in a culture environment incorporating such factors, and then determining whether the compound has increased the number of cardiomyocyte lineage cells in the population according to the phenotypic markers listed below.

Direct Differentiation

As already described, differentiation paradigms for pPS cells traditionally involve forming embryoid bodies, which allows cross-talk between different cell types, thought to promote tissue formation in a manner reminiscent of an embryo. However, it is often advantageous to eliminate the need to form embryoid bodies, allowing the differentiation process to be more controlled, and the resulting cell population tend to be more uniform (WO 01/51616; US 2002/0151053 A1). This disclosure provides new methods for direct differentiation of hES cells into cardiomyocytes, without forming embryoid bodies and without using serum or serum supplements.

An illustration of the direct differentiation technique is provided in Example 5. First, the pPS cells are harvested from the culture in which they are expanded (optimally feeder-free), and plated onto a substrate or matrix that is adherent for undifferentiated hES cells, and is compatible with cardiomyocyte differentiation. Exemplary are 0.5% gelatin, 20 μg/mL fibronectin, or Matrigel®. The substrate or matrix can be coated onto the surface of the culture vessel; or in some instances can be part of a particulate or meshwork support present throughout the culture environment. When gelatin is used, adherence of the cells can be promoted by preincubating the matrix with serum, and then washing away the serum before plating the cells. If desired, the pPS cells can be established onto the substrate before initiating differentiation—for example, by continuing to culture for a suitable time (say, 4 to 8 days) with a similar medium to what is used to expand the pPS cells in the undifferentiated form. This will typically bring the pPS cells to confluence as a monolayer in the new culture environment.

The differentiation process is initiated by culturing the plated cells in a medium that contains factors referred to elsewhere in this disclosure that promote cardiomyocyte differentiation. Exemplary are activins and/or bone morphogenic proteins. A combination of TGF-β superfamily proteins Activin A and BMP-4 is particularly effective (Example 5). In some circumstances, other morphogens like BMP-2 may substitute for BMP-4. The medium used at this stage or for later culture steps may contain adjuncts selected from the list provided earlier. Exemplary are insulin like growth factors, particularly IGF I, and/or a tumor necrosis factor or other inflammatory cytokine, particularly TNF-α. Culturing with the differentiation factors can take anywhere from a few days to several weeks or more to direct the cells into the cardiomyocyte lineage, with 4-7 days being typical.

One of the advantages of this technique is that a serum or serum substitute is not needed to initiate or support the cardiomyocyte differentiation process, as is typical of other methods. Instead, the medium can be formulated so that it contains an artificial nutritional supplement that supports differentiated cells like cardiomyocytes or neurons. Exemplary are B27 supplement, N2 supplement, and G5 supplement (Life Technologies/Gibco). Such supplements often comprise nutrients and cofactors like human insulin (500 μg/L), human transferrin (5-10 mg/mL), and selenium (0.5 μg/mL), and may also contain putrescine (1.5 mg/L), biotin (1 μg/L), hydrocortisone (0.4 μg/L), or progesterone (0.6 μg/L), and/or low levels of mitogens like EGF or FGF (1 μg/L). For purposes of commercial scale production and human therapy, elimination of components derived from non-human animals is particularly advantageous.

It has also been found that the proportion of cardiomyocyte lineage cells suitable for regenerative medicine can often be enhanced by withdrawing the TGF-β superfamily morphogens, and then continuing the culture for a few days or as many as 1 or 2 weeks or more in a similar supplemented medium. In this step, the medium sometimes can contain growth factors such as IGF, but BMP-2, other BMPs, or other morphogens may delay emergence of the cardiomyocyte phenotype and reduce yield.

Cardiomyocyte lineage cells (identified by marker expression or contraction activity) are ultimately harvested from the culture. The harvested population may contain over 5% or 10% Nkx2.5 positive cells.

Populations of differentiated cells can then be further processed to enrich cells with desirable characteristics, such as by mechanical separation or sorting for surface markers. For example, the percentage of contracting cells can be enriched up to ~20-fold by density separation. Isolation of enriched cardiomyocyte populations by isopycnic centrifugation is illustrated in Examples 1 and 4. Populations can be obtained that comprise at least ~5%, ~20%, ~60%, and potentially over ~90% cells of the cardiomyocyte lineage, identified by expression of MHC or other tissue specific marker. Many of the research and therapeutic applications referred to in this disclosure benefit from enrichment of the proportion of cardiomyocytes, but complete homogeneity is often not required.

Formation of Cardiac Bodies™

It also has been discovered that preparations of pPS derived cardiomyocytes can be further expanded or enriched by allowing them to grow in clusters that are referred to as Cardiac Bodies™.

First, a cell population is generated that contains cells with phenotype characteristics of cardiomyocyte lineage cells, and optionally enriched by density separation or other technique.

The cells are then allowed to form clusters, and single cells in the suspension are removed. This can be accomplished by letting the clusters settle, and pipetting out the supernatant containing single cells. Before proceeding, it is sometimes beneficial to break apart the clusters (for example, by brief trypsinization and/or mechanical dispersion). The cells are then cultured in suspension in low adhesion plates in fresh culture medium (exemplified by medium containing fetal bovine serum, serum substitute, or CCT as described earlier), and allowed to reaggregate into "secondary" Cardiac Bodies™. Culturing then continues with periodic refeeding, as necessary, with cardiomyocyte lineage cells remaining as clusters of 10 to 5000 cells (typically 50 to 1000 cells) in size.

After a suitable period (typically 1 to 7 days), the cultured cells can be harvested for characterization, or used in drug screening or pharmaceutical manufacture. The purification effect may improve if the cells are taken through further cycles of removing single cells and reculturing the clusters, over a period of 8 days or more. Each cycle can optionally incorporate a step in which the clusters of cells are dispersed into single cells, or smaller cell clusters, to allow for further expansion. Larger clusters may form, either by aggregation of the suspended cells, or by proliferation within the cluster, or both. It is a hypothesis of this invention that cardiomyocyte lineage cells have a tendency to form such clusters under appropriate conditions, and that the removal of single cells helps eliminate other cell types and increase homogeneity.

Examples 6 and 7 illustrate the process. Mixed populations of cells containing cardiomyocytes were put in fresh medium, and the clusters were harvested by settling in a 15 or 50 mL conical tube. They were refed in serum-containing medium, and taken through cycles of cluster separation, feeding, and reculturing every 2 or 3 days. After about 8 days, there was considerably increased expression of cardiomyocyte markers cTnI and MHC at the mRNA level (FIG. 7), and a high proportion of spontaneously contracting clusters (FIG. 8).

The Cardiac Body™ technique can be used to expand and/or enrich the cardiomyocytes in the cell population at any time in the differentiation process. As exemplified below, the technique can be used after a previous enrichment step by density separation. Implementation of the technique has benefits that were not anticipated before the making of this invention. In particular, the expression of myosin heavy chain detected by real-time PCR increases 10- to 100-fold when the cells are cultured for a 7 day period. A large proportion of the clusters in the composition exhibit spontaneous contractile activity: usually over 50%, and potentially between about 80% and 100% when processed in the manner described.

Characterization of Cardiomyocyte Lineage Cells

Figure 1:
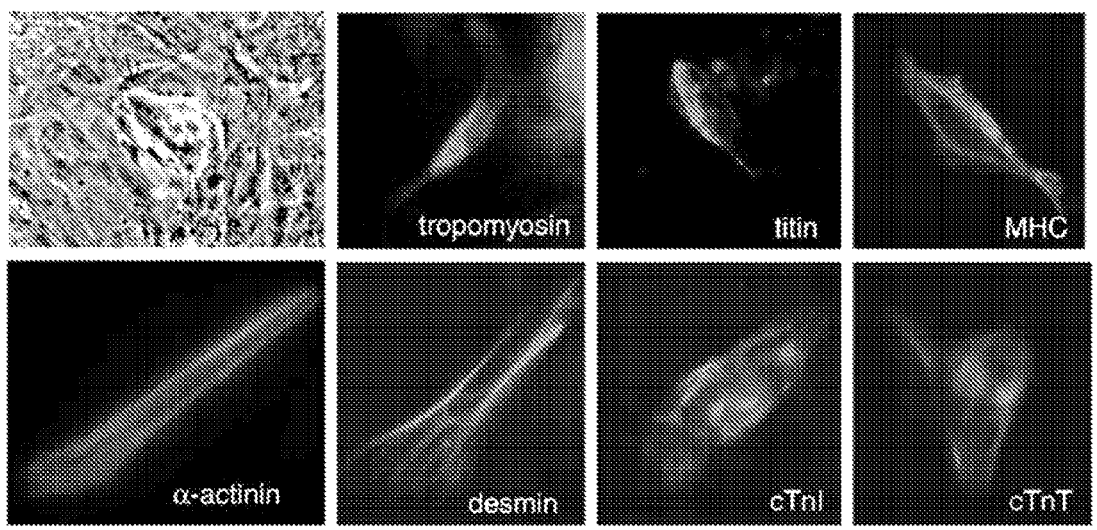

The cells obtained according to the techniques of this invention can be characterized according to a number of phenotypic criteria. Cardiomyocytes and precursor cells derived from pPS cell lines often have morphological characteristics of cardiomyocytes from other sources. They can be spindle, round, triangular or multi-angular shaped, and they may show striations characteristic of sarcomeric structures detectable by immunostaining (FIG. 1). They may form flattened sheets of cells, or aggregates that stay attached to the substrate or float in suspension, showing typical sarcomeres and atrial granules when examined by electron microscopy.

pPS derived cardiomyocytes and their precursors typically have at least one of the following cardiomyocyte specific markers:

Cardiac troponin I (cTnI), a subunit of troponin complex that provides a calcium-sensitive molecular switch for the regulation of striated muscle contraction Cardiac troponin T (cTnT)

Nkx2.5, a cardiac transcription factor expressed in cardiac mesoderm during early mouse embryonic development, which persists in the developing heart The cells will also typically express at least one (and often at least 3, 5, or more) of the following markers:

Atrial natriuretic factor (ANF), a hormone expressed in developing heart and fetal cardiomyocytes but down-regulated in adults. It is considered a good marker for cardiomyocytes because it is expressed in a highly specific manner in cardiac cells but not skeletal myocytes.

myosin heavy chain (MHC), particularly the β chain which is cardiac specific

Titin, tropomyosin, α-sarcomeric actinin, and desmin

GATA-4, a transcription factor that is highly expressed in cardiac mesoderm and persists in the developing heart. It regulates many cardiac genes and plays a role in cardiogenesis MEF-2A, MEF-2B, MEF-2C, MEF-2D; transcription factors that are expressed in cardiac mesoderm and persist in developing heart N-cadherin, which mediates adhesion among cardiac cells Connexin 43, which forms the gap junction between cardiomyocytes.

β1-adrenoceptor (β1-AR)

creatine kinase MB (CK-MB) and myoglobin, which are elevated in serum following myocardial infarction α-cardiac actin, early growth response-I, and cyclin D2.

Tissue-specific markers can be detected using any suitable immunological technique—such as flow immunocytometry or affinity adsorption for cell-surface markers, immunocytochemistry (for example, of fixed cells or tissue sections) for intracellular or cell-surface markers, Western blot analysis of cellular extracts, and enzyme-linked immunoassay, for cellular extracts or products secreted into the medium. Antibodies that distinguish cardiac markers like cTnI and cTnT from other isoforms are available commercially from suppliers like Sigma and Spectral Diagnostics. Expression of an antigen by a cell is said to be antibody-detectable if a significantly detectable amount of antibody will bind to the antigen in a standard immunocytochemistry or flow cytometry assay, optionally after fixation of the cells, and optionally using a labeled secondary antibody.

The expression of tissue-specific gene products can also be detected at the mRNA level by Northern blot analysis, dot-blot hybridization analysis, or by reverse transcriptase initiated polymerase chain reaction (RT-PCR) using sequence-specific primers in standard amplification methods using publicly available sequence data (GenBank). Expression of tissue-specific markers as detected at the protein or mRNA level is considered positive if the level is at least 2-fold, and preferably more than 10- or 50-fold above that of a control cell, such as an undifferentiated pPS cell or other unrelated cell type.

Once markers have been identified on the surface of cells of the desired phenotype, they can be used for immunoselection to further enrich the population by techniques such as immunopanning or antibody-mediated fluorescence-activated cell sorting.

Figure 2:
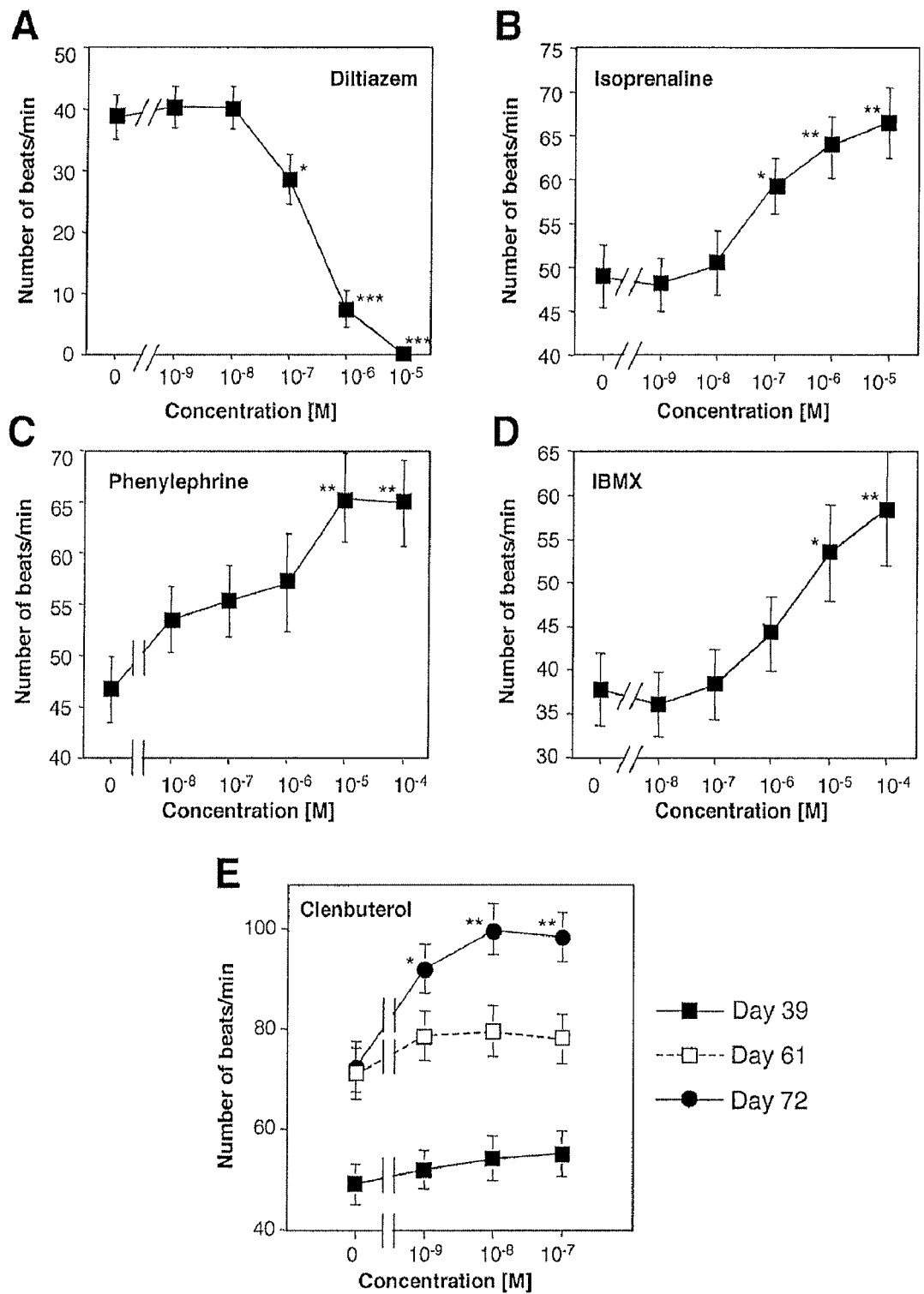

Under appropriate circumstances, pPS-derived cardiomyocytes often show spontaneous periodic contractile activity. This means that when they are cultured in a suitable tissue culture environment with an appropriate $Ca^{++}$ concentration and electrolyte balance, the cells can be observed to contract across one axis of the cell, and then release from contraction, without having to add any additional components to the culture medium. The contractions are periodic, which means that they repeat on a regular or irregular basis, at a frequency between ~6 and 200 contractions per minute, and often between ~20 and ~90 contractions per minute in normal buffer (FIG. 2). Individual cells may show spontaneous periodic contractile activity on their own, or they may show spontaneous periodic contractile activity in concert with neighboring cells in a tissue, cell aggregate, or cultured cell mass.

The contractile activity of the cells can be characterized according to the influence of culture conditions on the nature and frequency of contractions. Compounds that reduce available $Ca^{++}$ concentration or otherwise interfere with transmembrane transport of $Ca^{++}$ often affect contractile activity. For example, the L-type calcium channel blocker diltiazem inhibits contractile activity in a dose-dependent manner (FIG. 2). On the other hand, adrenoceptor agonists like isoprenaline and phenylephrine have a positive chronotropic effect. Further characterization of functional properties of the cell can involve characterizing channels for $Na^+$, $K^+$, and $Ca^{++}$. Electrophysiology can be studied by patch clamp analysis for cardiomyocyte like action potentials. See Igelmund et al., Pflugers Arch. 437:669, 1999; Wobus et al., Ann. N.Y. Acad. Sci. 27:752, 1995; and Doevendans et al., J. Mol. Cell Cardiol. 32:839, 2000.

Functional attributes provide a manner of characterizing cells and their precursors in vitro, but may not be necessary for some of the uses referred to in this disclosure. For example, a mixed cell population enriched for cells bearing some of the markers listed above, but not all of the functional or electrophysiology properties, can be of considerable therapeutic benefit if they are capable of grafting to impaired cardiac tissue, and acquiring in vivo the functional properties needed to supplement cardiac function.

Where derived from an established line of pPS cells, the cell populations and isolated cells of this invention can be characterized as having the same genome as the line from which they are derived. This means that the chromosomal DNA will be over 90% identical between the pPS cells and the cardiac cells, which can be inferred if the cardiac cells are obtained from the undifferentiated line through the course of normal mitotic division. The characteristic that cardiomyocyte lineage cells are derived from the parent cell population is important in several respects. In particular, the undifferentiated cell population can be used for producing additional cells with a shared genome—either a further batch of cardiac cells, or another cell type that may be useful in therapy—such as a population that can pre-tolerize the patient to the histocompatibility type of the cardiac allograft (US 2002/0086005 A1; WO 03/050251).

Genetic Alteration of Differentiated Cells

The cells of this invention can be made to contain one or more genetic alterations by genetic engineering of the cells either before or after differentiation (US 2002/0168766 A1). A cell is said to be "genetically altered" when a polynucleotide has been transferred into the cell by any suitable means of artificial manipulation, or where the cell is a progeny of the originally altered cell that has inherited the polynucleotide. For example, the cells can be processed to increase their replication potential by genetically altering the cells to express telomerase reverse transcriptase, either before or after they progress to restricted developmental lineage cells or terminally differentiated cells (US 2003/0022367 A1).

The cells of this invention can also be genetically altered in order to enhance their ability to be involved in tissue regeneration, or to deliver a therapeutic gene to a site of administration. A vector is designed using the known encoding sequence for the desired gene, operatively linked to a promoter that is either pan-specific or specifically active in the differentiated cell type. Of particular interest are cells that are genetically altered to express one or more growth factors of various types such as FGF, cardiotropic factors such as atrial natriuretic factor, cripto, and cardiac transcription regulation factors, such as GATA-4, Nkx2.5, and MEF2-C. Production of these factors at the site of administration may facilitate adoption of the functional phenotype, enhance the beneficial effect of the administered cell, or increase proliferation or activity of host cells neighboring the treatment site.

Use of Cardiomyocytes and their Precursors

This invention provides a method to produce large numbers of cells of the cardiomyocyte lineage. These cell populations can be used for a number of important research, development, and commercial purposes.

Drug Screening

Cardiomyocytes of this invention can be used commercially to screen for factors (such as solvents, small molecule drugs, peptides, oligonucleotides) or environmental conditions (such as culture conditions or manipulation) that affect the characteristics of such cells and their various progeny.

In some applications, pPS cells (undifferentiated or differentiated) are used to screen factors that promote maturation into later-stage cardiomyocyte precursors, or terminally differentiated cells, or to promote proliferation and maintenance of such cells in long-term culture. For example, candidate maturation factors or growth factors are tested by adding them to cells in different wells, and then determining any phenotypic change that results, according to desirable criteria for further culture and use of the cells.

Other screening applications of this invention relate to the testing of pharmaceutical compounds for their effect on cardiac muscle tissue maintenance or repair. Screening may be done either because the compound is designed to have a pharmacological effect on the cells, or because a compound designed to have effects elsewhere may have unintended side effects on cells of this tissue type. The screening can be conducted using any of the precursor cells or terminally differentiated cells of the invention.

The reader is referred generally to the standard textbook *In vitro Methods in Pharmaceutical Research*, Academic Press, 1997, and U.S. Pat. No. 5,030,015. Assessment of the activity of candidate pharmaceutical compounds generally involves combining the differentiated cells of this invention with the candidate compound, either alone or in combination with other drugs. The investigator determines any change in the morphology, marker phenotype, or functional activity of the cells that is attributable to the compound (compared with untreated cells or cells treated with an inert compound), and then correlates the effect of the compound with the observed change.

Cytotoxicity can be determined in the first instance by the effect on cell viability, survival, morphology, and the expression of certain markers and receptors. Effects of a drug on chromosomal DNA can be determined by measuring DNA synthesis or repair. [$^3$H]-thymidine or BrdU incorporation, especially at unscheduled times in the cell cycle, or above the level required for cell replication, is consistent with a drug effect. Unwanted effects can also include unusual rates of sister chromatid exchange, determined by metaphase spread. The reader is referred to A. Vickers (pp 375-410 in *In vitro Methods in Pharmaceutical Research*, Academic Press, 1997) for further elaboration.

Effect of cell function can be assessed using any standard assay to observe phenotype or activity of cardiomyocytes, such as marker expression, receptor binding, contractile activity, or electrophysiology—either in cell culture or in vivo. Pharmaceutical candidates can also be tested for their effect on contractile activity—such as whether they increase or decrease the extent or frequency of contraction. Where an effect is observed, the concentration of the compound can be titrated to determine the median effective dose ($ED_{50}$).

Animal Testing

This invention also provides for the use of cardiomyocytes and their precursors to enhance tissue maintenance or repair of cardiac muscle for any perceived need, such as an inborn error in metabolic function, the effect of a disease condition, or the result of significant trauma.

To determine the suitability of cell compositions for therapeutic administration, the cells can first be tested in a suitable animal model. At one level, cells are assessed for their ability to survive and maintain their phenotype in vivo. Cell compositions are administered to immunodeficient animals (such as nude mice, or animals rendered immunodeficient chemically or by irradiation). Tissues are harvested after a period of regrowth, and assessed as to whether pPS derived cells are still present.

This can be performed by administering cells that express a detectable label (such as green fluorescent protein, or β-galactosidase); that have been prelabeled (for example, with BrdU or [$^3$H]thymidine), or by subsequent detection of a constitutive cell marker (for example, using human-specific antibody). The presence and phenotype of the administered cells can be assessed by immunohistochemistry or ELISA using human-specific antibody, or by RT-PCR analysis using primers and hybridization conditions that cause amplification to be specific for human polynucleotides, according to published sequence data.

Suitability can also be determined by assessing the degree of cardiac recuperation that ensues from treatment with a cell population of pPS-derived cardiomyocytes. A number of animal models are available for such testing. For example, hearts can be cryoinjured by placing a precooled aluminum rod in contact with the surface of the anterior left ventricle wall (Murry et al., J. Clin. Invest. 98:2209, 1996; Reinecke et al., Circulation 100:193, 1999; U.S. Pat. No. 6,099,832; Reinecke et al., Circ Res., Epub March 2004). In larger animals, cryoinjury can be effected by placing a 30-50 mm copper disk probe cooled in liquid $N_2$ on the anterior wall of the left ventricle for ~20 min (Chiu et al., Ann. Thorac. Surg. 60:12, 1995). Infarction can be induced by ligating the left main coronary artery (Li et al., J. Clin. Invest. 100:1991, 1997). Injured sites are treated with cell preparations of this invention, and the heart tissue is examined by histology for the presence of the cells in the damaged area. Cardiac function can be monitored by determining such parameters as left ventricular end-diastolic pressure, developed pressure, rate of pressure rise, and rate of pressure decay.

Therapeutic Use in Humans

After adequate testing, differentiated cells of this invention can be used for tissue reconstitution or regeneration in a human patient or other subject in need of such treatment. The cells are administered in a manner that permits them to graft or migrate to the intended tissue site and reconstitute or regenerate the functionally deficient area. Special devices are available that are adapted for administering cells capable of reconstituting cardiac function directly to the chambers of the heart, the pericardium, or the interior of the cardiac muscle at the desired location.

Where desirable, the patient receiving an allograft of pPS derived cardiomyocytes can be treated to reduce immune rejection of the transplanted cells. Methods contemplated include the administration of traditional immunosuppressive drugs like cyclosporin A (Dunn et al., Drugs 61:1957, 2001), or inducing immunotolerance using a matched population of pPS derived cells (WO 02/44343; U.S. Pat. No. 6,280,718; WO 03/050251). Another approach is to adapt the cardiomyocyte cell population to decrease the amount of uric acid produced by the cells upon transplantation into a subject, for example, by treating them with allopurinol. Alternatively or in conjunction, the patient is prepared by administering allopurinol, or an enzyme that metabolizes uric acid, such as urate oxidase (PCT/US04/42917).

Patients suitable for receiving regenerative medicine according to this invention include those having acute and chronic heart conditions of various kinds, such as coronary heart disease, cardiomyopathy, endocarditis, congenital cardiovascular defects, and congestive heart failure. Efficacy of treatment can be monitored by clinically accepted criteria, such as reduction in area occupied by scar tissue or revascularization of scar tissue, and in the frequency and severity of angina; or an improvement in developed pressure, systolic pressure, end diastolic pressure, Δpressure/Δtime, patient mobility, and quality of life.

The cardiomyocytes of this invention can be supplied in the form of a pharmaceutical composition, comprising an isotonic excipient prepared under sufficiently sterile conditions for human administration. When the differentiation procedure has involved culturing the cells as Cardiac Bodies™, it may be desirable to disperse the cells using a protease or by gentle mechanical manipulation into a suspension of single cells or smaller clusters. To reduce the risk of cell death upon engraftment, the cells may be treated by heat shock or cultured with ~0.5 U/mL erythropoietin ~24 hours before administration.

For general principles in medicinal formulation, the reader is referred to *Cell Therapy: Stem Cell Transplantation, Gene Therapy*, and *Cellular Immunotherapy*, by G. Morstyn & W. Sheridan eds, Cambridge University Press, 1996; and *Hematopoetic Stem Cell Therapy*, E. D. Ball, J. Lister & P. Law, Churchill Livingstone, 2000. Choice of the cellular excipient and any accompanying elements of the composition will be adapted in accordance with the route and device used for administration. The composition may also comprise or be accompanied with one or more other ingredients that facilitate the engraftment or functional mobilization of the cardiomyocytes. Suitable ingredients include matrix proteins that support or promote adhesion of the cardiomyocytes, or complementary cell types, especially endothelial cells.

This invention also includes a reagent system, comprising a set or combination of cells that exist at any time during manufacture, distribution, or use. The cell sets comprise any combination of two or more cell populations described in this disclosure, exemplified but not limited to a type of differentiated pPS-derived cell (cardiomyocytes, cardiomyocyte precursors, Cardiac Bodies™, and so on), in combination with undifferentiated pPS cells or other differentiated cell types, often sharing the same genome. Each cell type in the set may be packaged together, or in separate containers in the same facility, or at different locations, at the same or different times, under control of the same entity or different entities sharing a business relationship.

Pharmaceutical compositions of this invention may optionally be packaged in a suitable container with written instructions for a desired purpose, such as the reconstitution of cardiomyocyte cell function to improve a disease condition or abnormality of the cardiac muscle.

The following examples are provided as further non-limiting illustrations of particular embodiments of the invention.

EXAMPLES

Example 1

Differentiation of hES Cells to Cardiomyocytes hES cell lines, H1, H7, H9, and H9.2 (a cloned line derived from H9) were initially established on feeder cells and later maintained under feeder-free conditions, as described in WO 01/51616. Differentiation was initiated by culturing hES cells in suspension to form embryoid bodies. After four days in suspension culture, the EBs were transferred to gelatin-coated plates or chamber slides. Beating cardiomyocytes were isolated from EB outgrowth mechanically at differentiation day 15-29, harvested, and washed. All hES cell lines tested had the potential to generate beating cardiomyocytes, even after being maintained for over 50 passages (~260 population doublings), although some lines (e.g., H7) generated more than others.

FIG. 1 shows immunocytochemistry of cells suspended using Collagenase B and replated, then stained for expression of sarcomeric myosin heavy chain (MHC), titin, tropomyosin, α-sarcomeric actinin, desmin, cTnI and cardiac troponin T (cTnT). Single cells and clusters stained positive for all these markers. The stained single cardiomyocytes were spindle, round and tri- or multi-angular shaped. The striations characteristic of the sarcomeric structures is also seen, consistent with the contractile apparatus necessary for muscle function.

Cardiomyocytes were further enriched by density separation on a discontinuous gradient of Percoll™ (a density separation medium comprising colloidal PVP-coated silica). Cardiomyocytes were generated as before, harvested after 15 days plated on gelatin, and resuspended in the differentiation medium. After settling for 5 min, the cell suspension was loaded onto a layer of 40.5% Percoll™ (Pharmacia) (~1.05 g/mL) overtop of a layer of 58.5% Percoll™ (~1.075 g/mL). The cells were then centrifuged at 1500 g for 30 min. After centrifugation, cells at the interface of the two layers were harvested, washed, resuspended in differentiation medium, and seeded into chamber slides. The harvested cells showed 26.8±4.1% staining for sarcomeric myosin heavy chain (MHC), which is at least ~20-fold higher than the starting cell population.

The function of hES-derived cardiomyocytes was tested by determining whether the cardiomyocytes respond appropriately to the chronotropic effects of cardioactive drugs.

FIG. 2 (Panel A) shows that the beating rate was inhibited by the L-type calcium blocker diltazem in a concentration-dependent manner. When cells were treated with $10^{-5}$ M diltiazem, 100% of the beating areas stopped contraction. This observation shows that the hES-derived cardiomyocytes have functional L-type calcium channels. Panels B and C show that there are positive chronotropic effects induced by isoprenaline (a β-adrenoceptor agonist) and phenylephrine (an α-adrenoceptor agonist). Panels D and E show that the phosphodiesterase inhibitor IBMX and the β2-adrenoceptor agonist clenbuterol have a similar effect. Thus, the hES cell derived cells respond to cardioactive drugs in a manner appropriate for cells of the cardiomyocyte lineage.

Example 2

Factors that Promote Cardiomyocyte Differentiation

Embryoid bodies from the H1 or H9 line were treated at differentiation day 1-4, 4-6 or 6-8 with 5-aza-deoxy-cytidine, a cytosine analog that affects DNA methylation. Cells were harvested at day 15, and analyzed for cardiac MHC by real-time RT-PCR. One to 10 μM of 5-aza-deoxy-cytidine at day 6-8 significantly increased the expression of cardiac α-MHC, correlating with an increased proportion of beating areas in the culture.

Other reagents examined for an ability to induce cardiomyocyte differentiation included dimethyl sulfoxide (DMSO) and all-trans retinoic acid (RA). Embryoid bodies treated with 0.5% DMSO from days 0-4 produced fewer beating areas than non-treated cultures. Beating cells were absent from cultures treated with 0.8% or 1% DMSO, and 1.5% DMSO was actually toxic to the cells. DMSO treatment also caused significant reduction in α-MHC expression, compared with untreated cultures.

Retinoic acid was applied to differentiating hES cultures at doses between $10^{-9}$ and $10^{-5}$ M. At day 0-4, the RA was toxic to the cells, while at days 4-8, 8-15, or 4-15, there was no increase in beating cells compared with untreated cultures. Thus, 5-aza-deoxy-cytidine increased the proportion of cardiomyocyte cells in the population. In contrast, DMSO and retinoic acid inhibit cardiomyocyte differentiation, even though these compounds generate cardiomyocytes from mouse embryonic carcinoma or embryonic stem cells (Wobus et al., J. Mol. Cell Cardiol. 29:1525, 1997; McBurney et al., Nature 299:165, 1982).

Example 3

Effective Combinations of Cardiomyocyte Differentiation Agents

This example is an investigation of combined effects of added growth factors to influence cardiomyocyte differentiation of human ES cells.

The rationale was as follows. Group I factors were selected as being able to supply functions of the hypoblast during initial commitment. Group II factors were selected as able to supply functions of endoderm during subsequent development in combination with Group I factors. Group III factors were selected as survival factors for cardiomyocytes in extended culture. A typical working concentration was defined as "medium" level, with 4-fold lower and 4-fold higher levels defined as "low" and "high" levels, The concentrations are shown below:

TABLE 2

Exemplary Cardiotropic Factors

| Growth Factor | Low concentration | Medium concentration | High concentration |
|---|---|---|---|
| Group I | | | |
| Activin A | 6.25 ng/mL | 25 ng/mL | 100 ng/mL |
| TGF β1 | 2.5 ng/mL | 10 ng/mL | 40 ng/mL |
| IGF II | 6.25 nM | 25 nM | 100 nM |

TABLE 2-continued

Exemplary Cardiotropic Factors

| Growth Factor | Low concentration | Medium concentration | High concentration |
|---|---|---|---|
| Group II | | | |
| BMP 4 | 1.25 ng/mL | 5 ng/mL | 20 ng/mL |
| FGF 4 | 12.5 ng/mL | 50 ng/mL | 200 ng/mL |
| Insulin | 6.25 ng/mL | 25 ng/mL | 100 ng/mL |
| bFGF | 12.5 ng/mL | 50 ng/mL | 200 ng/mL |
| PDGF-BB | 12.5 ng/mL | 50 ng/mL | 200 ng/mL |
| 5-aza-deoxy-cytidine | 10 µM | 10 µM | 10 µM |
| Group III | | | |
| IGF I | 6.25 nM | 25 nM | 100 nM |
| IGF II | 6.25 nM | 25 nM | 100 nM |
| LIF | 5 ng/mL | 20 ng/mL | 80 ng/mL |
| EGF | 6.25 ng/mL | 25 ng/mL | 100 ng/mL |
| PDGF-BB | 0.9 ng/mL | 3.6 ng/mL | 14.4 ng/mL |
| bFGF | 2.5 ng/mL | 10 ng/mL | 40 ng/mL |
| Insulin | 6.25 nM | 25 nM | 100 nM |

Figure 3:
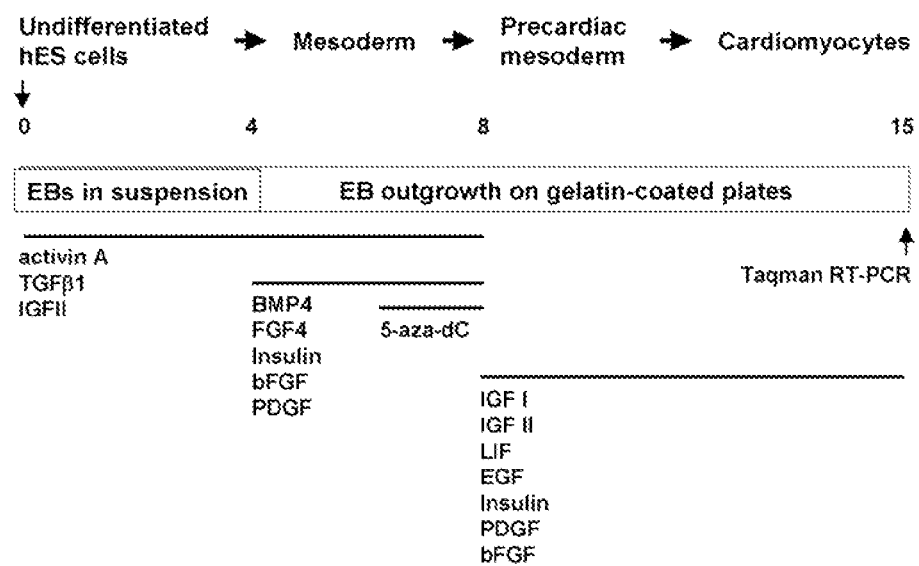
Figure 3:
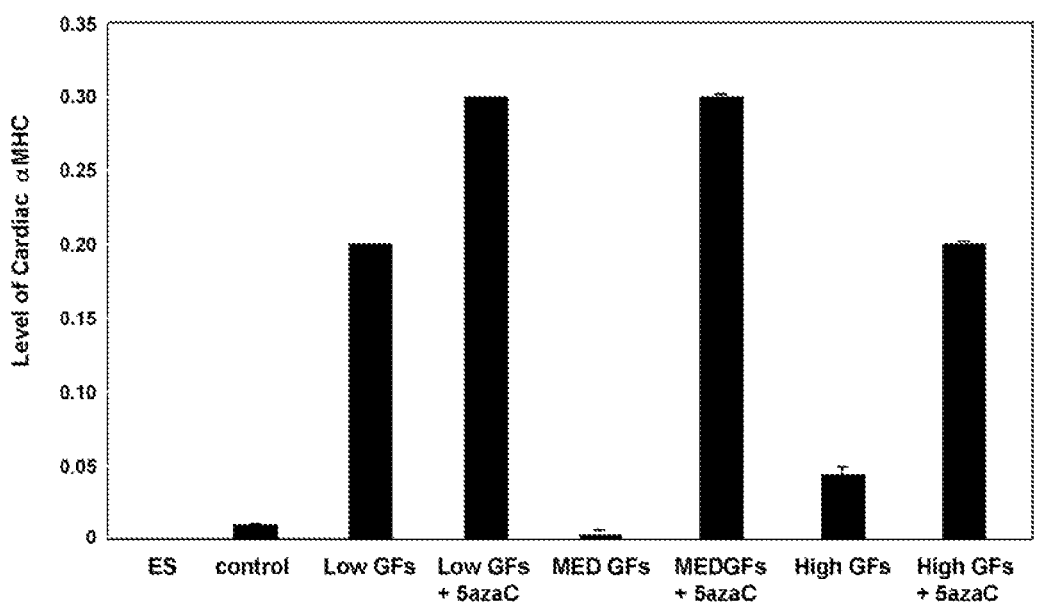

FIG. 3 (Upper Panel) shows the scheme for use of these factors. H1 cells at passage 48 were used to generate embryoid bodies by collagenase treatment followed by mechanically dislodging the cells from the dish by scraping with a 5 mL pipet. The contents of one 10 cm$^2$ well of cells was transferred to a single 10 cm$^2$ well of a low adherence plate and cultured in 4 ml of DMEM plus 20% FBS in the presence or absence of additional factors for 4 days. At the end of day 4, each suspension of embryoid bodies was divided into 2 aliquots plated in 2 wells of a gelatin-coated adherent 6 well tissue culture plate (10 cm$^2$/well). The adherent embryoid bodies and their outgrowths were cultured in 4 mL of DMEM plus 20% FBS in the presence or absence of additional factors for 11 days, after which the number of beating regions in each well was observed by light microscopy, and RNA was harvested from each well for subsequent quantitative PCR analysis.

Group I factors were added on day 0, (the day on which undifferentiated cells were transferred to suspension culture to generate embryoid bodies) and were present continuously until day 8 (4 days after the embryoid bodies were plated in gelatin-coated wells). Group II factors were added on day 4 (at the time of plating) and were present continuously until day 8. Group III factors were added on day 8 and were present continuously until the end of the experiment (day 15). A subset of cultures was exposed to 5-aza-deoxy-cytidine for 48 hrs (day 6-8). Cultures were re-fed with fresh media plus or minus factors on days 6, 8, 11, and 13.

It was observed that while no beating regions were observed in the control cultures (those maintained in the absence of supplementary factors/5-aza-deoxy-cytidine) or those maintained in the presence of the growth factors in the absence of 5-aza-deoxy-cytidine, beating areas were observed in all wells receiving the combination of growth factors plus 5-aza-deoxy-cytidine.

FIG. 3 (Lower Panel) shows quantitative PCR analysis (Taqman™) for expression of the cardiac gene a myosin heavy chain (αMHC), relative to the level in normal heart RNA. The level of expression was significantly higher in cells exposed to growth factors (GF) plus 5-aza-deoxy-cytidine. The lowest concentrations tested were sufficient to achieve higher αMHC expression (30-fold higher than the levels seen in control.

These results were elaborated in a subsequent experiment. H1 cells (passage 38) were cultured as before, except that: a) only the lowest concentrations of factors used in the previous experiment were employed; and b) in one set of samples, the Group III treatment was omitted. The level of marker expression was then determined in real-time PCR assay relative to undifferentiated cells.

Figure 4A:
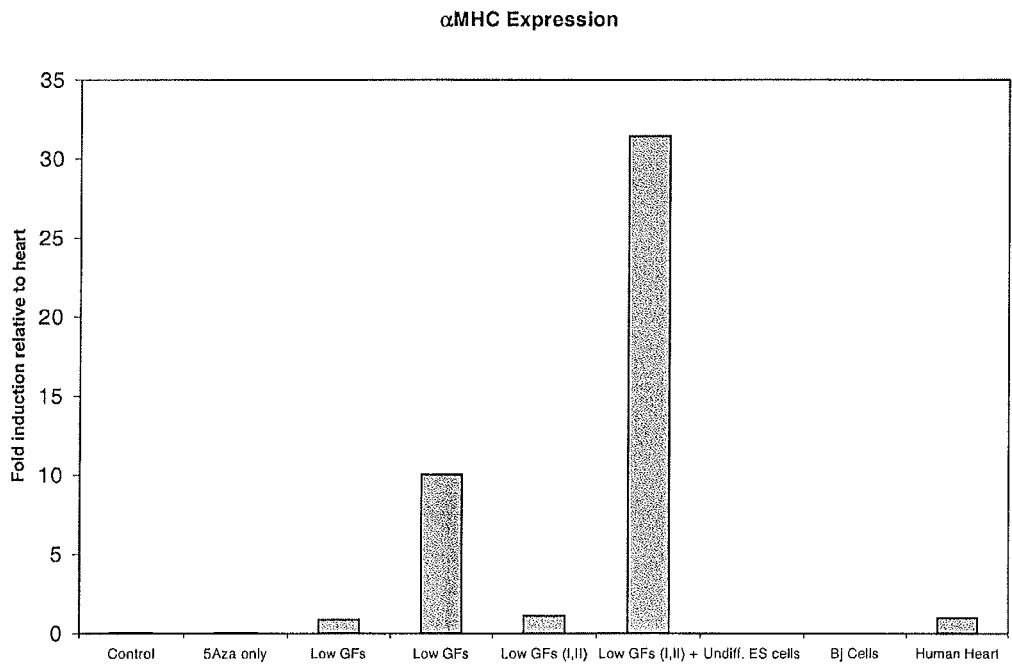
Figure 4A:
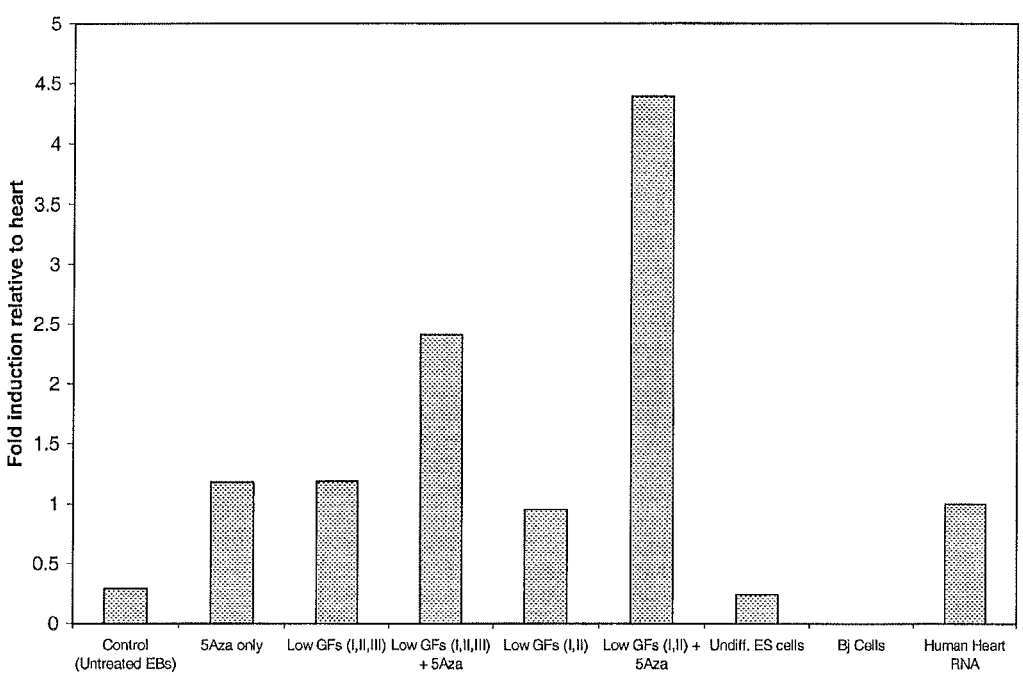
Figure 4B:
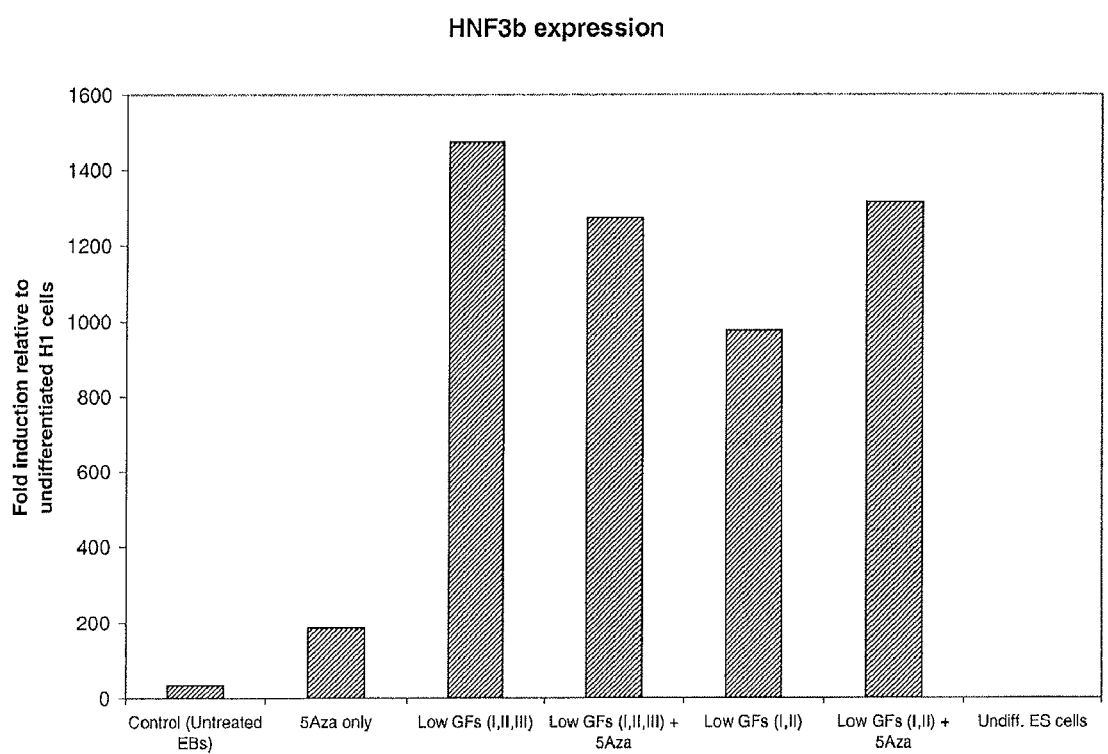

FIG. 4 shows that omission of Group III from the protocol led to a further 3-fold increase in the amount of αMHC mRNA expression. Increases in the expression of the early cardiomyocyte-associated gene GATA-4 were also detected. In contrast, the endoderm-associated gene HNF3b is not specifically induced under these conditions. The effect on α-MHC and GATA-4 was selective, in comparison with the endoderm-associated gene HNF3b, which increased using any growth factor combination, but not with 5-aza-deoxy-cytidine.

These results demonstrate that factors within Groups I and II enhance the proportion of cells bearing characteristic features of cardiomyocytes.

Example 4

Four-Phase Centrifugation Separation Method

Cardiomyocytes were generated from hES cells of the H7 line by forming embryoid bodies for 4 days, and then proliferating on gelatin-coated plates for 17 days (5-aza-deoxy-cytidine and growth factors were not used). The cells were then dissociated using collagenase B, resuspended in differentiation medium. The cell suspension was then layered onto a discontinuous gradient of Percoll™, and centrifuged at 1500 g for 30 min. Four fractions were collected: I. The upper interface; II. The 40.5% layer; III. The lower interface; IV. The 58.5% layer. The cells were washed and resuspended in differentiation medium. Cells for immunostaining were seeded into chamber slides at $10^4$ cells per well, cultured for 2 or 7, and then fixed and stained.

Results are shown in Table 3. Percentage of MHC positive cells was determined by counting cells in 30 images from triplicate wells for each fraction and presented as mean±standard deviation of cells from 3 wells.

TABLE 3

Percoll ™ Separation

| | | | % staining for MHC | |
|---|---|---|---|---|
| Fraction | Cell Count | Beating Cells | Day 2 | Day 7 |
| Before separation | | + | 17 ± 4.4% | 15 ± 4% |
| I | 9.0 × 10$^6$ | ± | 2.6 ± 0.5% | 2.5 ± 3.0% |
| II | 1.6 × 10$^6$ | + | 4.5 ± 1.5% | 2.4 ± 0.9% |
| III | 4.0 × 10$^6$ | ++ | 35.7 ± 2.7% | 28.3 ± 9.4% |
| IV | 1.3 × 10$^6$ | +++ | 69. ± 5.0% | 52.2 ± 14.5% |

Beating cells were observed in all fractions, but Fractions III and IV contained the highest percentage.

Phenotype of the cells as determined by indirect immunocytochemistry is shown in Table 4.

TABLE 4

Characteristics of Separated Cell Populations

| Epitope | Cardiomyocyte lineage | Non-cardiac cells |
|---|---|---|
| cTnl | ++ | − |
| cardiac-specific α/β MHC | ++ | − |
| cardiac β MHC | ++ | − |
| sarcomeric MHC | ++ | − |
| N-cadherin | ++ | ± |
| smooth muscle actin | ++ | subset |

TABLE 4-continued

Characteristics of Separated Cell Populations

| Epitope | Cardiomyocyte lineage | Non-cardiac cells |
|---|---|---|
| myogenin | − | − |
| α-fetoprotein | − | − |
| β-tubulin III | − | − |
| Ki67 | subset | subset |
| BrdU | subset | subset |
| SSEA-4 | − | − |
| Tra-1-81 | − | − |

Cardiomyocyte populations separated by density gradient centrifugation could be distinguished by staining for cTnI and MHC. Absence of staining for myogenin, α-fetoprotein, or β-tubulin III showed the absence of skeletal muscle, endoderm cell types, and neurons. Lack of staining for SSEA-4 and Tra-1-81 confirms the absence of undifferentiated hES cells.

α-Smooth muscle actin (SMA) is reportedly present in embryonic and fetal cardiomyocytes, but not adult cardiomyocytes (Leor et al., Circulation 97:I1332, 1996; Etzion et al., Mol. Cell Cardiol. 33:1321, 2001). Virtually all cTnI-positive cells and a subset of cTnI negative cells obtained in the cardiomyocyte differentiation protocol were positive for SMA, suggesting that they may be at an early stage and capable of proliferation.

Cells in fraction III and IV were replated, cultured for an additional 2 days. 43±4% of the MHC positive cells expressed BrdU, indicating that they were in the S phase of the cell cycle. In other experiments, a subset of cTnI-positive cells were found to express Ki-67. These results show that about 20% or 40% of the cardiomyocytes in the population were undergoing active proliferation.

Example 5

Direct Differentiation Protocol

In this example, hES cells of the H7 line were differentiated into cardiomyocyte lineage cells by plating onto a substrate and culturing in a serum-free medium containing differentiation factors.

Tissue culture surfaces were prepared by coating overnight with 0.5% gelatin, then incubating for 2 to 4 h with medium containing 20% FBS, which was removed prior to plating of the hES cells. Alternatively, the plastic was coated with human fibronectin (20 μg/mL) or growth factor-reduced Matrigel® with no subsequent incubation with serum-containing medium.

In an exemplary trial, TGF-β related factors were tested for their ability to induce expression of genes characteristic of mesoderm or early stage cardiomyocytes. Undifferentiated hES cells from the H7 line were seeded into 24 well gelatin coated plates. After one week of growth in mEF conditioned medium as undifferentiated cells, the medium was changed to RPMI+B27 supplement, with or without 50 ng/mL Activin A, 50 ng/mL BMP-4, or both factors together. After four days, the growth factors were removed by medium exchange, and the cells were then cultured for an additional 14 days in RPMI+B27 alone. For comparison, hES cells were also differentiated by the embryoid body protocol as already described (culturing four days suspended in medium containing 20% FBS, then on 0.5% gelatin-coated surfaces, and harvesting at day 12-20 of culture).

Expression of α-myosin heavy chain in the differentiated cells was determined by real-time PCR analysis using gene-specific primers. Data were normalized by multiplex reactions with the 18s rRNA-specific assay from Applied Biosystems.

Figure 5A:
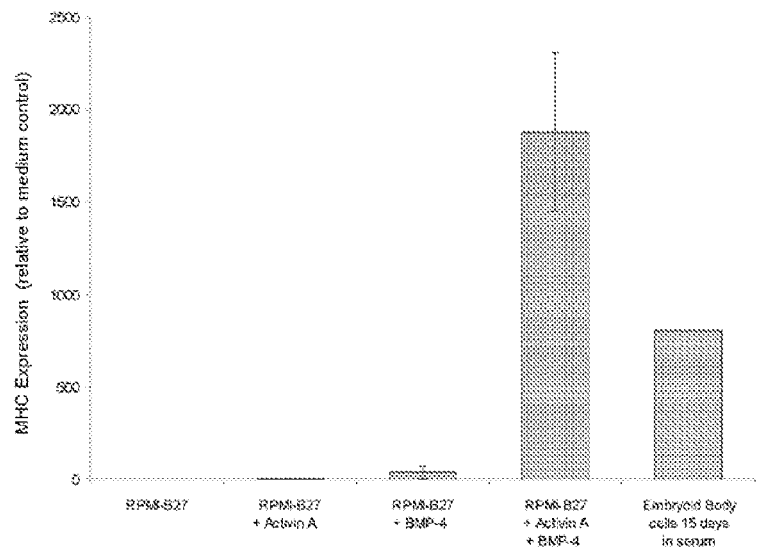

FIG. 5(A) shows the results. The combination of Activin A and BMP-4 in the direct differentiation method on gelatin coated plates produced cells expressing considerably higher levels of MHC, compared with cells generated from embryoid bodies in serum-containing medium. Numerous spontaneously beating areas were evident, forming spheres that later took on a more flattened appearance and began to beat 7 days after withdrawing Activin A and BMP-4. No such beating areas were evident in wells cultured without Activin A and BMP-4.

In a separate trial, cells were differentiated in the same fashion on multiwell chamber slides. Multiple spontaneously beating areas were evident in wells cultured with using Activin A and BMP-4, showing evidence of organized, functional sarcomeres, whereas no beating areas were present in wells cultured in the absence of the factor combination. The slides were fixed with 2% paraformaldehyde, permeabilized with ethanol, and then stained for marker expression.

Figure 5B:
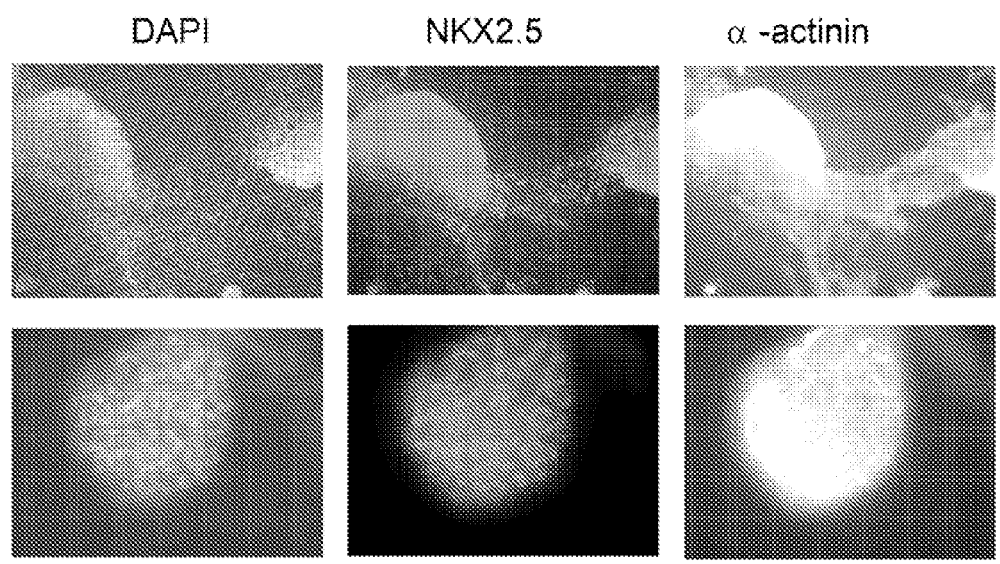

FIG. 5(B) shows the results. The cells demonstrated both strong nuclear-localized expression of the cardiac transcription factor Nkx2.5, and cytoplasmic expression of α-sarcomeric actinin. Clusters of cells were observed that stained for both markers. Separate positively staining cells had organized striated patterns of α-actinin, consistent with functional sarcomeres. Similar results were obtained using the H1 line of hES cells.

In another experiment, cardiomyocytes were generated from the H7 line of hES cells previously expanded in the undifferentiated form in fresh (non-conditioned) medium. The defined medium was made from commercially obtained XVIVO-10™ (BioWhittaker), as described in US 2005/0037492 A1, supplemented with 2 mM L-glutamine, 0.1 mM 2-mercaptoethanol, 0.1 mM non-essential amino acids (invitrogen), 80 ng/mL bFGF and 0.5 ng/mL TGFβ1.

The first step was to plate hES cells onto matrix suitable for cardiomyocyte generation. Confluent H7 hES cells maintained in the defined medium were incubated with collagenase IV (200 U/mL) at 37° C. for 5 min, washed with PBS, harvested as small clusters, and plated onto gelatin coated chamber slides or 24 well plates (coated with 0.5% gelatin overnight, then incubated with FBS containing medium overnight). The cells were cultured on the new matrix for two days in medium containing 20% FBS, 1 mM L-glutamine, 0.1 mM 2-mercaptoethanol and 0.1 mM non-essential amino acids followed by XVIVO-10™ medium, followed by four days in XVIVO-10™ medium containing 8 or 80 mg/mL bFGF and 0.5 ng/mL TGFβ1 for 6 days; or for six days in the supplemented XVIVO-10™ medium.

To differentiate into cardiomyocytes, the plated cells were next cultured in RPMI medium supplemented with B27, 50 ng/mL BMP-4 and 50 ng/mL Activin A. The medium was replaced after four days with RPMI medium supplemented with B27, but lacking the growth factors.

Cells at differentiation day 18 were harvested for immunocytochemical analysis, They were fixed in PBS containing 2% paraformaldehyde, permeabilized with ethanol, blocked with 10% normal goat serum, and then incubated with antibody against Nkx2.5 (Santa Cruz Biotech) or α-sarcomeric actinin (Sigma), followed by labeled secondary antibody.

Figure 6:
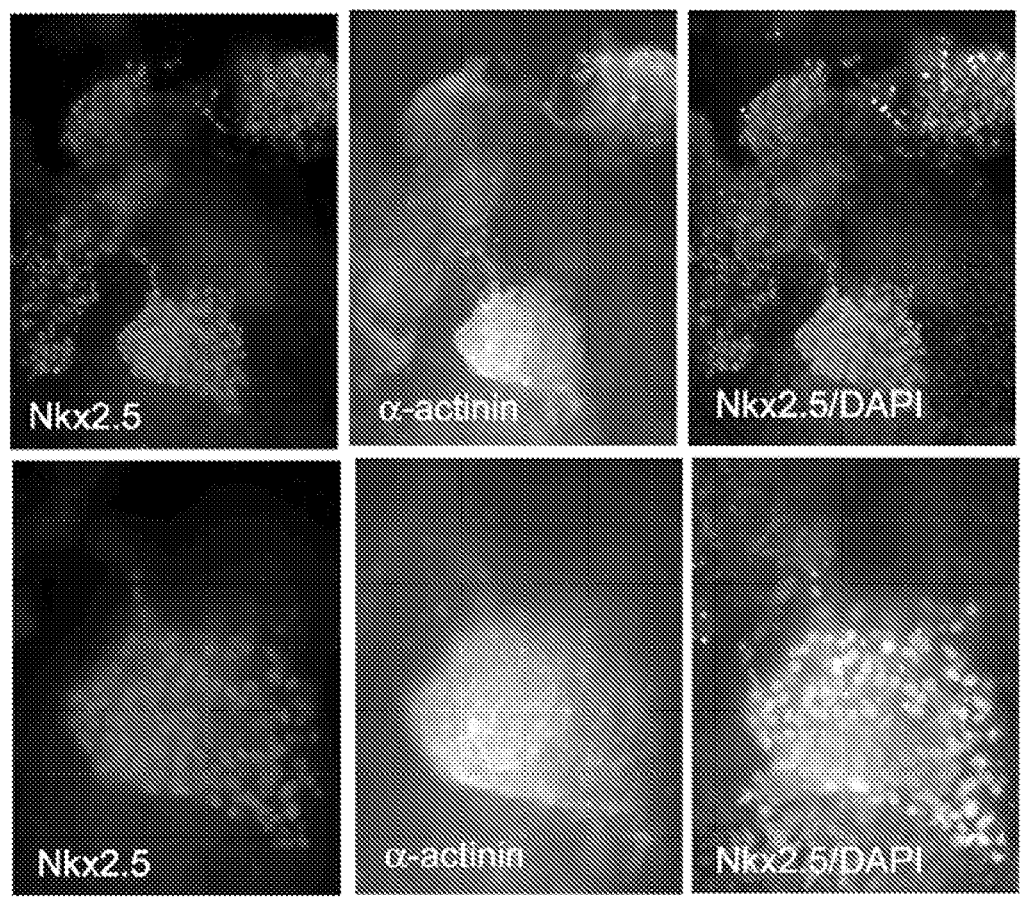
FIG. 6 is taken from an experiment in which the hES cells were expanded in defined medium before being used to make the cardiomyocytes by direct differentiation.

FIG. 6 shows the results. Cardiac lineage cells were identified by expression of both Nkx2.5 in the nuclei and α-sarcomeric actinin in the cytoplasm. Some of the cells present expressed Nkx2.5 in the nuclei but were negative for α-actinin expression, which is believed to represent cardiomyocyte precursors cells. Both the double positive cells and the Nkx2.5 positive/α-actinin negative cells were present as cell clumps of various sizes.

The direct differentiation method produces large numbers of beating cells arise that are suitable for both in vitro studies and transplantation. The surprising efficiency and ease of cardiomyocyte generation in this system implies a high proportion of cardiomyocyte progenitors, which is valuable for certain aspects of commercial scale cardiomyocyte production, and the use of these cells for drug screening and therapy.

Example 6

Enrichment of Contracting Cells by Making Cardiac Bodies™

This example illustrates the subsequent culturing of cardiomyocyte clusters as Cardiac Bodies™ to enrich for cells having characteristics desirable for therapeutic use and other purposes.

Three 225 cm² flasks of undifferentiated hES cells of the H7 line were used to generate embryoid bodies as already described. The EBs from each flask were resuspended in 75 mL of medium and transferred to three low adhesion six well plates (4 mL cell suspension per well), yielding nine plates of EBs in suspension in total. The EBs were re-fed after one day in suspension by transferring the newly formed EBs to 50 mL conical tubes (one plate per tube), letting the EBs settle at room temperature without agitation for 10 to 20 min, then removing the medium and replacing with fresh medium (25 mL per tube).

The EBs were returned to their original low attachment plates and maintained in suspension in 20% FBS containing medium for 3 additional days, then transferred to a total of three gelatin-coated 225 cm² tissue culture flasks. Two days after transfer to the gelatin coated flasks, the medium was removed and each flask was re-fed with 75 mL 20% FBS containing medium. Similar re-feedings occurred on day 8, 11, 13, 15, and 18. On day 20, the differentiated cultures were dissociated with Blendzyme™ and fractionated on discontinuous Percoll™ gradients as before. Fraction IV (the highest density fraction) was recovered and counted, yielding ~3.7×10⁶ single cells and small clusters.

The Fraction IV cells were resuspended in ~6.5 mL of 20% FBS containing medium, transferred to a 15 mL conical tube, and allowed to settle at room temperature without agitation for 10 min. The medium (containing 2.8×10⁶ cells, which is most of the single cells) was removed and replaced with fresh medium. The cell suspension was transferred to a single low attachment six well plate (~4 mL of cell suspension per well). The CBs were re-fed in a similar manner (transfer to 50 mL tube, settling for 10 min, medium removal and replacement) every 48 h.

Figure 7:
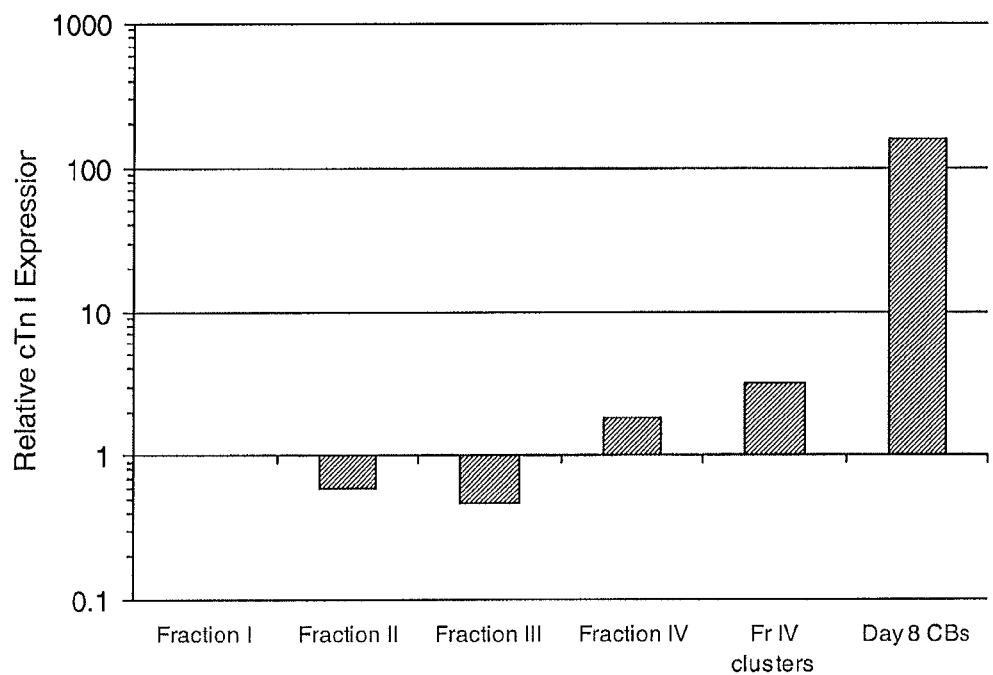
FIG. 7 shows the expression of cTnI measured in Cardiac Bodies™ formed from each of the four Percoll™ fractions.
Figure 7:
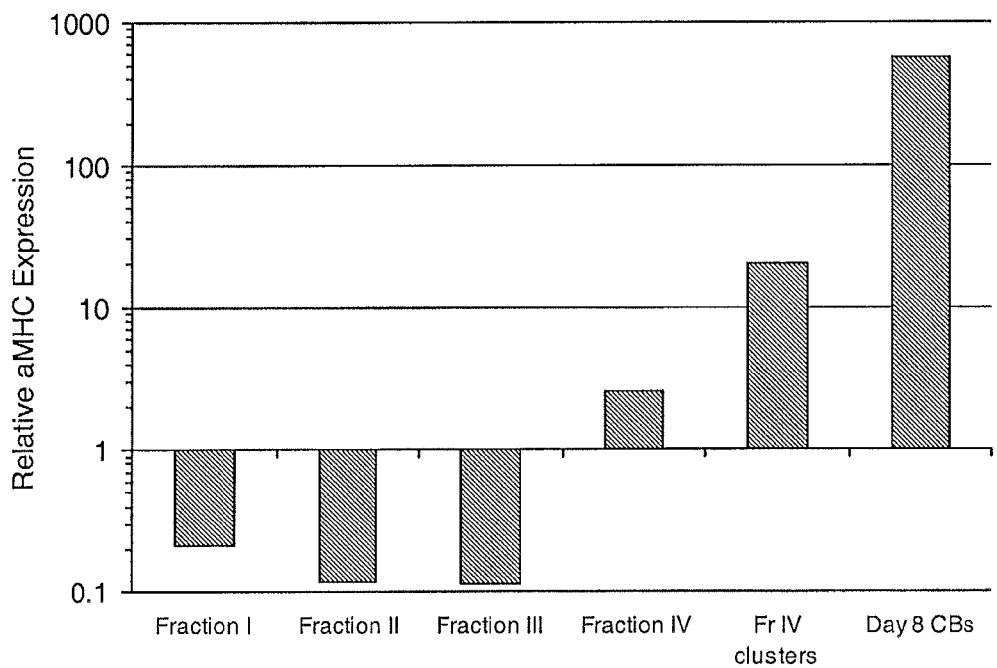

FIG. 7 shows the expression of the sarcomeric genes αMHC and cardiac troponin I as measured by real-time PCR (Taqman™). Relative to the expression after 20 days of culture on gelatin, separating the cells by Percoll™ increased expression by 2-5 fold in Fraction IV cells. Removing the single cells and collecting clusters increased expression to 5-20 fold. After 8 days of culturing the cells as Cardiac Bodies™, the expression was 100- to 500-fold higher than the unseparated cells.

When CBs are replated onto gelatin or Matrigel® (isolated basement membrane produced by Engelbreth-Holm-Swarm tumor cells and containing extracellular matrix components such as laminin), the clusters adhere, flatten, and produce large patches of spontaneously contracting cells. For use in animal testing, the Cardiac Bodies™ may be implanted directly, or dispersed into suspensions of single cells.

Example 7

Comparison of Culture Conditions

In this example, the cardiomyocyte differentiation culture was conducted for different periods before Percoll™ separation and Cardiac Body™ formation.

Seven 225 cm² flasks of undifferentiated hES cells were used to generate EBs, yielding 21 plates of EBs in suspension in total. As before, the EBs were cultured in 20% fetal bovine serum, plated onto gelatin on day 4, and refed with fresh medium every 2 or 3 days thereafter. On day 12, four flasks of differentiated cells were separated by density gradient centrifugation as before, and on day 20, the remaining 3 flasks were processed. Clustered cells in each of the four Percoll™ fractions were separated into single cell suspensions. They were then grown in suspension culture to form Cardiac Bodies™, fed with fresh medium on days 2, 5, and 6. On day 7, they were harvested and viewed under the microscope.

FIG. 8(A) shows a field of Cardiac Bodies™ made from Fraction IV cells (bar=300 μm). The clusters marked by the arrows were undergoing spontaneous contractions. FIG. 8(B) shows the quantitative data obtained by counting the contracting clusters in each preparation. Fraction IV showed the highest proportion of spontaneously contracting cells, and was higher when the starting population had been differentiated for 20 days. Using a similar protocol, suspensions have been obtained in which most of the clusters were beating.

It was found that the percentage of cardiac cells in Cardiac Bodies™ can be increased as follows: after the Percoll™ gradient separation and removal of single cells from the fraction IV clusters, the clusters are dissociated to a single cell suspension by trypsinizing and resuspending in culture medium (20% FBS-containing medium or preferably a serum-free medium containing a serum substitute, or CCT). The suspension is transferred to low-adhesion 6 well plates (4 mL/well) and cultured with re-feeding every 2-3 days. The resultant "secondary" Cardiac Bodies™ that form show a higher percentage of cardiomyocytes (45.9%, determined by flow cytometry for cTNT-positive cells) compared with the clusters that formed initially (14.1%).

In subsequent experiments, Cardiac Bodies™ were analyzed for phenotypic markers, with the following results.

TABLE 4

Characteristics of Cardiac Bodies ™

| Epitope | Cardiomyocyte lineage | Non-cardiac cells |
|---|---|---|
| cTnI | ++ | – |
| cTnT | ++ | – |
| α-actinin | ++ | – |
| sarcomeric MHC | ++ | – |
| CD56 | ++ | subset |
| Pan-cytokeratins | – | subset |

The techniques of direct differentiation and cardiac bodyT™ formation can be combined to optimize purity and yield of cardiomyocyte lineage cells. Exemplary is the following procedure.

Undifferentiated hES cells are plated onto tissue culture plates or flasks that have been pretreated with Matrigel®, human fibronectin, or 0.5% gelatin, preincubated with FBS. Cells are expanded either with mEF conditioned medium, or with XVIVO-10™ medium supplemented with 100 ng/mL bFGF and 0.5 ng/mL TGFβ1). After 1 week, the medium is replaced with RPMI plus a supplement like B27, and 50 ng/mL each of Activin A and BMP-4. Four days later, the medium is replaced with RPMI plus supplement without the Activin or BMP. Cultures are fed every 2 or 3 days with the same medium until the cell harvest (typically ~14 days after the removal of activin and BMP-4).

Cells are harvested and purified by Blendzyme™ digestion and centrifugation through a discontinuous Percoll™ gradient. Fraction IV cells are resuspended at a concentration corresponding to approximately 1-5 million cells/mL and transferred to a conical tube. The cell suspension is incubated at room temperature for 10 min without agitation. The floating cells are removed by gentle aspiration and the remaining clusters are washed once with PBS and then dissociated to single cells with 0.025% trypsin/EDTA. The cells are resuspended in 20% FBS-containing medium at approximately 4 mL per 5 million starting Fraction IV cells. The cell suspension is transferred to low adhesion tissue culture plates and re-fed every 2 to 4 days by gently centrifuging or letting the Cardiac Bodies™ settle at room temp prior to replacement of the medium. The Cardiac Bodies™ can be used as an enriched source of hES-derived cardiomyocytes after 1-2 weeks of suspension culture, or subject to further rounds of Cardiac Body™ formation before harvesting.

Example 8

Transplantation of Cardiac Bodies™ into the Intact Myocardium

To assess the ability of cardiac bodies to survive in vivo, H7-derived cells were implanted into uninjured hearts of adult nude rats. H7 hES cells were used to generate embryoid bodies in 20% FBS-containing medium; the embryoid bodies were cultured in suspension for 4 days, and then allowed to adhere to gelatin-coated flasks, where they were cultured for 2 additional weeks. Cardiac Bodies™ were prepared as described above, and maintained in suspension in 20% FBS-containing medium for 1 week with re-feeding every 2-3 days.

The implantation experiments were done by Drs. Charles Murry and Michael Laflamme at the University of Washington in Seattle, under a Sponsored Research Agreement with Geron Corp. Twenty-four hours prior to implantation, the Cardiac Bodies™ were subjected to 30 minute heat shock at 43° to increase survival. On the day of implantation, Cardiac Bodies™ were injected into the left ventricular myocardium of uninjured nude rats. After 1 week, the rats were sacrificed, the hearts were fixed, sectioned, and examined for the presence of human cells in the myocardium.

FIG. 9 shows the results. Human cells were identified in two out of three of the rats on the basis of in situ hybridization with a human-specific pancentromeric probe (middle panel). The human cells were further identified as cardiomyocytes by labeling with an antibody directed against β-myosin heavy chain and specific for the human ortholog (lower panel).

These data demonstrate that the hES derived cardiomyocyte lineage cells of this invention are suitable for transplantation into the myocardium, where they survive and integrate into the host tissue.

The Compositions and Procedures Provided in the Description can be Effectively Modified by Those Skilled in the Art without Departing from the Invention Embodied in the Claims that Follow

What is claimed in the invention is:

1. A method of differentiating a primate pluripotent stem (pPS) cell into a cell expressing α-MHC comprising a) plating the undifferentiated pPS cell without forming an embryoid body directly onto a solid surface comprising a substrate; b) contacting the pPS cell plated on the solid surface with one of the following: 1) BMP; or 2) activin and BMP; c) culturing the contacted pPS cell of b), thereby directing differentiation of the pPS cell into a cell expressing α-MHC.

2. The method of claim 1, wherein the pPS cell is cultured serum-free in steps b) and c).

3. The method of claim 1, wherein the pPS cell is contacted with BMP.

4. The method of claim 1, wherein the pPS cell is contacted with activin and BMP.

5. The method of claim 1, wherein the substrate is produced by Engelbreth-Holm-Swarm tumor cells.

6. The method of claim 1, wherein the substrate is gelatin.

7. A method of differentiating a primate pluripotent stem (pPS) cell into a cell expressing Nkx2.5 comprising a) plating the undifferentiated pPS cell without forming an embryoid body directly onto a solid surface comprising a substrate; b) contacting the pPS cell with activin and BMP; c) culturing the contacted pPS cell of b), thereby directing differentiation of the pPS cell into a cell expressing Nkx2.5.

8. The method of claim 7, wherein the pPS cell is cultured serum-free in steps b) and c).

9. The method of claim 7, wherein the substrate is produced by Engelbreth-Holm-Swarm tumor cells.

10. The method of claim 7, wherein the substrate is gelatin.

11. A method of differentiating a primate pluripotent stem (pPS) cell into a cell expressing α-sarcomeric actinin comprising a) plating the undifferentiated pPS cell without forming an embryoid body directly onto a solid surface comprising a substrate; b) contacting the pPS cell with activin and BMP; c) culturing the contacted pPS cell of b), thereby directing differentiation of the pPS cell into a cell expressing α-sarcomeric actinin.

12. The method of claim 11, wherein the pPS cell is cultured serum-free in steps b) and c).

13. The method of claim 11, wherein the substrate is produced by Engelbreth-Holm-Swarm tumor cells.

14. The method of claim 11, wherein the substrate is gelatin.

* * * * *